US011426111B2

(12) United States Patent
Olson

(10) Patent No.: US 11,426,111 B2
(45) Date of Patent: Aug. 30, 2022

(54) VARIABLE DENSITY MAPPING CATHETER

(71) Applicant: St. Jude Medical, Cardiology Division, Inc., St. Paul, MN (US)

(72) Inventor: Gregory K. Olson, Elk River, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 671 days.

(21) Appl. No.: 16/293,200

(22) Filed: Mar. 5, 2019

(65) Prior Publication Data

US 2019/0282116 A1  Sep. 19, 2019

Related U.S. Application Data

(60) Provisional application No. 62/642,413, filed on Mar. 13, 2018.

(51) Int. Cl.
*A61B 5/287* (2021.01)
*A61B 18/14* (2006.01)
*A61B 5/00* (2006.01)
*A61B 34/20* (2016.01)
*A61B 18/00* (2006.01)

(52) U.S. Cl.
CPC ............ *A61B 5/287* (2021.01); *A61B 5/6859* (2013.01); *A61B 18/1492* (2013.01); *A61B 34/20* (2016.02); *A61B 2018/00267* (2013.01); *A61B 2018/00351* (2013.01); *A61B 2018/00577* (2013.01); *A61B 2018/00702* (2013.01); *A61B 2018/00791* (2013.01);
(Continued)

(58) Field of Classification Search
CPC ... A61B 5/287; A61B 5/6859; A61B 18/1492; A61B 2018/00267; A61B 2018/1475; A61B 2018/00351; A61B 2018/1467; A61B 2018/00839; A61B 2018/00577; A61B 2018/00375
See application file for complete search history.

(56) References Cited

U.S. PATENT DOCUMENTS 4,522,212 A  6/1985  Gelinas et al.
5,702,438 A  12/1997  Avitall
(Continued)

FOREIGN PATENT DOCUMENTS

AU  2015202258 B2  6/2016
AU  2016204351 A1  1/2017
(Continued)

OTHER PUBLICATIONS

Magtibay et al., JAHA 2017 (J Am Heart Assoc. 2017; 6:e006447. DOI:10.1161/JAHA.117.0076447 (pp. 6-7 and section titled Omnipoles Provide the Largest Possible Bipolar Voltages.).
(Continued)

*Primary Examiner* — Eun Hwa Kim
(74) *Attorney, Agent, or Firm* — Kilpatrick Townsend & Stockton LLP

(57) ABSTRACT

Aspects of the present disclosure are directed to flexible high-density mapping catheters with a high-density array of mapping electrodes. These mapping catheters may be used to detect electrophysiological characteristics of tissue in contact with the electrodes, and may be used to diagnose cardiac conditions, such as cardiac arrhythmias for example.

8 Claims, 11 Drawing Sheets

(52) U.S. Cl.
CPC .............. *A61B 2018/00839* (2013.01); *A61B 2018/1467* (2013.01); *A61B 2018/1475* (2013.01)

(56) References Cited

U.S. PATENT DOCUMENTS

| | | | |
|---|---|---|---|
| 5,964,757 | A | 10/1999 | Ponzi |
| 6,029,091 | A | 2/2000 | de la Rama et al. |
| 6,071,282 | A | 6/2000 | Fleischman |
| 6,123,699 | A | 9/2000 | Webster, Jr. |
| 6,171,277 | B1 | 1/2001 | Ponzi |
| 6,183,463 | B1 | 2/2001 | Webster, Jr. |
| 6,198,974 | B1 | 3/2001 | Webster, Jr. |
| 6,210,407 | B1 | 4/2001 | Webster |
| 6,231,570 | B1 | 5/2001 | Tu et al. |
| 6,267,746 | B1 | 7/2001 | Bumbalough |
| 6,415,187 | B1 | 7/2002 | Kuzma et al. |
| 6,522,932 | B1 | 2/2003 | Kuzma et al. |
| 6,652,515 | B1 | 11/2003 | Maguire et al. |
| 6,658,302 | B1 | 12/2003 | Kuzma et al. |
| 6,961,602 | B2 | 11/2005 | Fuimaono et al. |
| 7,027,851 | B2 | 4/2006 | Mejia |
| 7,089,045 | B2 | 8/2006 | Fuimaono et al. |
| 7,099,712 | B2 | 8/2006 | Fuimaono et al. |
| 7,155,270 | B2 | 12/2006 | Solis et al. |
| 7,228,164 | B2 | 6/2007 | Fuimaono et al. |
| 7,257,435 | B2 | 8/2007 | Plaza |
| 7,302,285 | B2 | 11/2007 | Fuimaono et al. |
| 7,412,274 | B2 | 8/2008 | Mejia |
| 7,429,261 | B2 | 9/2008 | Kunis et al. |
| 7,561,907 | B2 | 7/2009 | Fuimaono et al. |
| 8,187,267 | B2 | 5/2012 | Pappone et al. |
| 8,206,404 | B2 | 6/2012 | de la Rama et al. |
| 8,271,099 | B1 | 8/2012 | Swanson |
| 8,391,947 | B2 | 3/2013 | Urman et al. |
| 8,486,063 | B2 | 7/2013 | Werneth et al. |
| 8,565,894 | B2 | 10/2013 | Vetter et al. |
| 8,603,069 | B2 | 12/2013 | Selkie |
| 8,744,599 | B2 | 6/2014 | Tegg |
| 9,044,245 | B2 | 6/2015 | Condie et al. |
| 9,820,664 | B2 | 11/2017 | Hoitink et al. |
| 9,907,480 | B2 | 3/2018 | Basu et al. |
| 9,949,656 | B2 | 4/2018 | Wu et al. |
| 10,285,610 | B2 | 5/2019 | Wu |
| 10,578,737 | B2 | 3/2020 | Gliner et al. |
| 10,702,177 | B2 | 7/2020 | Aujla |
| 2005/0159741 | A1 | 7/2005 | Paul et al. |
| 2009/0198300 | A1 | 8/2009 | Zhang et al. |
| 2010/0152731 | A1 | 6/2010 | de la Rama et al. |
| 2010/0174177 | A1 | 7/2010 | Wu |
| 2010/0286684 | A1 | 11/2010 | Hata et al. |
| 2011/0118582 | A1 | 5/2011 | De La Rama et al. |
| 2011/0118726 | A1 | 5/2011 | de la Rama et al. |
| 2011/0288392 | A1 | 11/2011 | de la Rama et al. |
| 2011/0313417 | A1 | 12/2011 | De La Rama et al. |
| 2012/0010490 | A1 | 1/2012 | Kauphusman et al. |
| 2012/0271302 | A1 | 10/2012 | Behl et al. |
| 2012/0296232 | A1 | 11/2012 | Ng |
| 2013/0085479 | A1 | 4/2013 | de la Rama et al. |
| 2013/0253504 | A1 | 9/2013 | Fang |
| 2013/0274582 | A1 | 10/2013 | Afonso et al. |
| 2014/0200639 | A1* | 7/2014 | De La Rama ....... A61N 1/0476 607/116 |
| 2014/0257069 | A1 | 9/2014 | Eliason et al. |
| 2014/0296902 | A1 | 10/2014 | Huszar et al. |
| 2014/0316496 | A1 | 10/2014 | Masson et al. |
| 2014/0350564 | A1 | 11/2014 | Huszar et al. |
| 2015/0105645 | A1* | 4/2015 | Subramaniam ........ A61B 5/361 600/374 |
| 2015/0141785 | A1 | 5/2015 | Hayam et al. |
| 2015/0159741 | A1 | 6/2015 | Versteyhe et al. |
| 2015/0351652 | A1 | 12/2015 | Marecki et al. |
| 2015/0374252 | A1 | 12/2015 | de la Rama et al. |
| 2016/0143588 | A1* | 5/2016 | Hoitink ................ A61B 5/6859 600/374 |
| 2016/0213916 | A1 | 7/2016 | de la Rama |
| 2016/0317094 | A1 | 11/2016 | Byrd et al. |
| 2016/0374753 | A1 | 12/2016 | Wu et al. |
| 2017/0000365 | A1 | 1/2017 | Wu et al. |
| 2017/0042449 | A1* | 2/2017 | Deno ................ A61M 25/0127 |
| 2017/0112404 | A1 | 4/2017 | de la Rama et al. |
| 2017/0112405 | A1 | 4/2017 | Sterrett et al. |
| 2017/0319269 | A1 | 11/2017 | Oliverius et al. |
| 2017/0360369 | A1* | 12/2017 | Geist ....................... A61B 5/01 |
| 2017/0367756 | A1 | 12/2017 | Sliwa et al. |
| 2018/0042667 | A1 | 2/2018 | Pappone et al. |
| 2018/0050190 | A1 | 2/2018 | Masson |
| 2018/0056038 | A1 | 3/2018 | Aujla |
| 2018/0070845 | A1 | 3/2018 | Hoitink et al. |
| 2018/0116539 | A1 | 5/2018 | Olson et al. |
| 2018/0193089 | A1 | 7/2018 | Wu |
| 2019/0110750 | A1 | 4/2019 | Dahlen et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 | 12/2016 |
| CA | 2934211 A1 | 12/2016 |
| CA | 2934214 A1 | 12/2016 |
| CN | 101797181 B | 12/2015 |
| CN | 105960201 B | 9/2016 |
| CN | 106264715 A | 1/2017 |
| CN | 106264716 A | 1/2017 |
| CN | 106308790 A | 1/2017 |
| EP | 2664295 A1 | 11/2013 |
| EP | 2732843 B1 | 5/2014 |
| EP | 2752153 A1 | 7/2014 |
| EP | 3111871 B1 | 3/2018 |
| EP | 2907462 B1 | 9/2018 |
| EP | 3023052 B1 | 3/2019 |
| EP | 3114987 A1 | 8/2020 |
| IL | 246415 A | 12/2019 |
| JP | 2017012750 A | 1/2017 |
| JP | 2017012755 A | 1/2017 |
| JP | 2017038919 A | 2/2017 |
| WO | 2015057521 A1 | 4/2015 |
| WO | 2015095577 A1 | 6/2015 |
| WO | 2015130824 A1 | 9/2015 |
| WO | 2016001015 A1 | 1/2016 |

OTHER PUBLICATIONS

Haldar et al., Circulation AE @017 (Circ Arrhythm Electrophysiol. 2017; 10:e005018. DOI: 10/1161/CIRCEP.117.005018 (p. 6, Omnipolar Voltage Amplitude Correlates to Largest Measurable Bipolar Vpp., and Figure 4.).

\* cited by examiner

VARIABLE DENSITY MAPPING CATHETER

CROSS-REFERENCE TO RELATED APPLICATIONS

This application claims priority to U.S. provisional application No. 62/642,413, filed 13 Mar. 2018, which is hereby incorporated by reference as though fully set forth herein.

BACKGROUND a. Field

The instant disclosure relates to high-density mapping catheters for diagnosing, for example, cardiac arrhythmias. In particular, the instant disclosure relates to flexible planar catheters or basket catheters including a plurality of electrodes positioned in a high-density array.

b. Background Art

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), metallic electrodes, especially when sharp gradients and undulations are present.

When mapping a cardiac muscle, the beating of the heart, especially if erratic or irregular, makes it difficult to keep adequate contact between electrodes and tissue for a sufficient length of time. These problems are exacerbated on contoured, irregular, or trabeculated surfaces. If the contact between the electrodes and the tissue cannot be sufficiently maintained, quality lesions or accurate mapping are unlikely to result.

During electrophysiology mapping, a clinician may require two mapping catheters to fully diagnose a cardiac condition such as an arrhythmia and/or to verify an efficacy of a treatment regimen. A clinician may use a global mapping catheter to conduct a general electrophysiology mapping of a cardiac chamber (e.g., left atrium). For areas of interest (e.g., pulmonary veins), the clinician may further use a regional mapping catheter to conduct a more granular electrophysiology mapping of the area of interest.

The foregoing discussion is intended only to illustrate the present field and should not be taken as a disavowal of claim scope.

BRIEF SUMMARY

The instant disclosure relates to high-density mapping catheters for diagnosing, for example, cardiac arrhythmias. In particular, the instant disclosure relates to both planar and basket type end effectors coupled to a distal end of a catheter shaft. The planar and basket type end effectors may include an array of electrodes to facilitate electrophysiology mapping of tissue in contact with the electrodes. Various embodiments of the present disclosure are directed to flexible, mapping catheters with adjustable electrode array densities. The variable electrode array density facilitates desired granularity of the electrophysiology map.

Aspects of the present disclosure are directed to a planar array catheter including an elongated catheter shaft and a flexible, planar array. The elongated catheter shaft includes a proximal end and a distal end, and defines a longitudinal axis. The flexible, planar array is coupled to the distal end of the catheter shaft. The planar array conforms to tissue, and includes two or more struts extending substantially parallel with the longitudinal axis and lying in a common plane. Each of the struts have a plurality of electrodes mounted thereon. The planar array has an adjustable relative spacing between the struts and thereby a variable areal density of the plurality of electrodes. In more specific embodiments, the planar array operates in a first configuration where the plurality of electrodes are equally spaced along both a length of each strut and across adjacent struts, and a second configuration where the spacing of the electrodes across adjacent struts is increased.

Some embodiments of the present disclosure are directed to a basket catheter that includes an elongated catheter shaft, a flexible basket catheter, and a plurality of electrodes. The elongated catheter shaft includes a proximal end and a distal end. The flexible basket catheter includes a plurality of splines, and is coupled to the distal end of the catheter shaft and conforms to tissue. The plurality of electrodes are mounted to the splines. The basket catheter has adjustable relative spacing between the splines and thereby a variable areal density of the plurality of electrodes. In specific embodiments, the splines operate in a global electrophysiology mapping configuration with the plurality of splines equally distributed circumferentially about a longitudinal axis of the catheter, and a regional electrophysiology mapping configuration with the plurality of splines unevenly distributed circumferentially about the longitudinal axis of the catheter.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which.

Figure 1A:
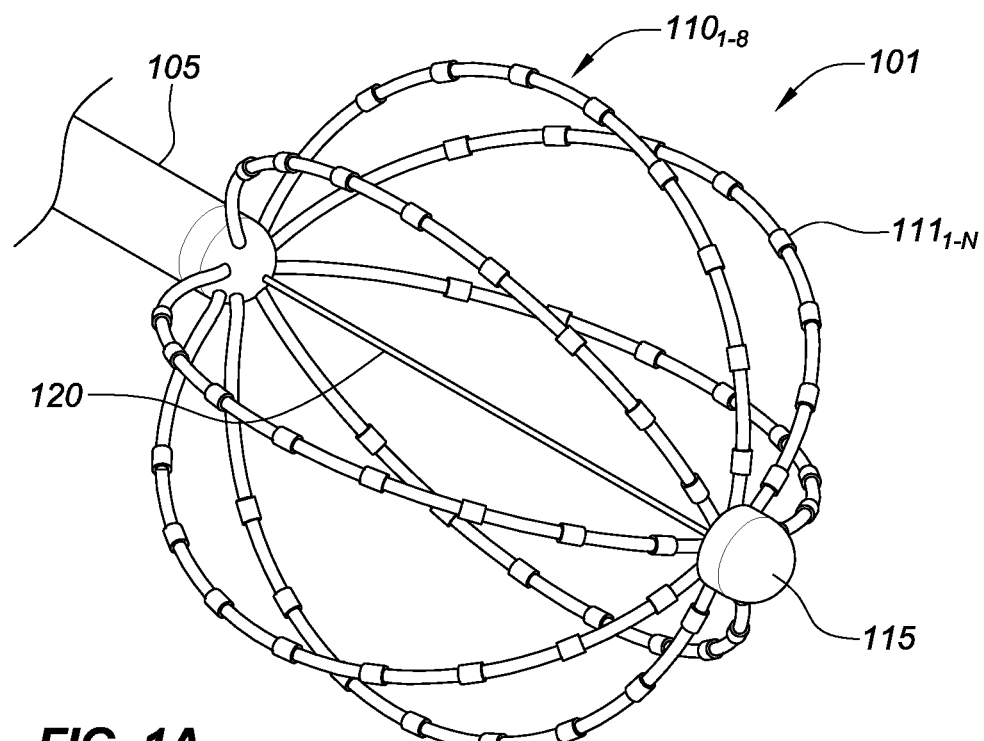
FIG. 1A is an isometric side view of a basket end effector of an electrophysiology catheter configured for global mapping, consistent with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to high-density mapping catheters for diagnosing, for example, cardiac arrhythmias. In particular, the instant disclosure relates to both planar and basket type end effectors coupled to a distal end of a catheter shaft. The planar and basket type end effectors may include an array of electrodes to facilitate electrophysiology mapping of tissue in contact with the electrodes. Various embodiments of the present disclosure are directed to flexible, mapping catheters with adjustable electrode array densities. The variable electrode array density facilitates variable granularity of an electrophysiology map.

In existing electrophysiology mapping basket catheters, splines comprising the basket are fixed radially relative to adjacent splines with respect to a longitudinal axis. The inter-spline spacing of electrodes is substantially controlled by expansion size of the basket and/or tissue contact related deflection. Moreover, the inter-spline electrode spacing may further be dependent upon the extent of deployment from a sheath. In these cases, the clinician has minimal control of the radial spacing of the splines or the resulting spacing between inter-spline electrode pairs. As a result, a clinician may not be able to generate an electrophysiology map with either the desired granularity or global frame. Aspects of the present disclosure facilitate clinician controlled rotation of one or more of the splines within a basket catheter about a longitudinal axis. By controlling the relative position of one or more of the splines within the basket catheter, the clinician may create high-density and/or low-density electrode regions across the basket catheter. For example, in some applications it may be desirable to acquire additional electrophysiology information between splines. By moving an additional spline therebetween, mapping fidelity is greatly improved. Moreover, such basket catheter adjustability may further benefit advanced electrophysiology mapping implementations such as orientation independent sensing/omnipolar technology (which is discussed in more detail below).

While some embodiments of a basket catheter in accordance with the present disclosure may have all of the splines of the basket independently movable relative to the other splines, the adjustability of one or two splines with the remaining splines being static may be sufficient for many finer granularity electrophysiology mapping applications. Once the splines of the basket catheter are placed into a high-density configuration, a clinician may maneuver the high-density region of the basket catheter into contact with target tissue for enhanced mapping.

In yet other embodiments, individual splines of the basket catheter may not be adjustable. Instead, the splines may be unevenly distributed circumferentially to create high and low density electrode array regions. To conduct a global electrophysiology mapping of a cardiac chamber, for example, electrodes on only certain splines of the basket may be sampled (e.g., electrodes on the splines which are evenly distributed about the basket). In use, a clinician may rotate the basket catheter to orient a high-density electrode array region of the basket catheter with a tissue region of interest to conduct a regional electrophysiology mapping.

Further embodiments of the present disclosure are directed to electrophysiology mapping catheters such as planar arrays. In such embodiments, struts of the planar array may be laterally adjustable to facilitate variable electrode array density. For example, a central strut of the planar array may facilitate a pull wire that extends between a distal portion of the planar array and a catheter handle. In response to actuation by a clinician, the pull wire draws the distal portion of the planar array proximally, causing the struts to bulge laterally outward from a static position. As a result, the intra-electrode spacing across the struts is increased facilitating global electrophysiology map. Where a regional map with enhanced fidelity is desired, the pull wire may be released and the planar array will return to its static configuration with decreased intra-electrode spacing across adjacent struts.

To conduct an electrophysiology mapping of a cardiac muscle, pacing is conducted. During the pacing procedure, adjacent electrodes are assigned to bipole pairings, and each bipole pair samples the electrical characteristics of the tissue in between the pair. The resulting electrical signals are received and processed by controller circuitry. The controller circuitry develops an electrophysiology mapping by associating the signal samples from each bipole pair with a location of the tissue sampled by the bipole pair. The electrogram from each bipole pair may be analyzed and various electrical characteristics may be visually indicated on an electrophysiology map by color-coding (or other visual indication scheme, e.g., shading, patterning, etc.). In some embodiments, the color-coding may be based on the electrogram voltage at each location (e.g., mean, average, max, etc.). In other embodiments, the number of times the electrical signal exceeds a threshold voltage (or a voltage slope changes signs) during a sampling window may be visually displayed on the map. In yet other embodiments, total energy sampled during a time window may be displayed. Various other methods of fractionation accounting are known, and may be used as one or more factors of the resulting color-code displayed on the electrophysiology map.

Aspects of the present disclosure are directed toward electrophysiology mapping catheters with adjustable, but known, spacing between electrodes which form bipole pairs for electrophysiology mapping. More advanced embodiments of the present disclosure may utilize orientation independent sensing/omnipolar technology ("OIS/OT") and related algorithms. OIS/OT and related algorithms are discussed in more detail in U.S. provisional application No. 61/944,426, filed 25 Feb. 2014, U.S. application Ser. No. 15/118,522, filed 25 Feb. 2015, and international application no. PCT/US2014/011940, filed 16 Jan. 2014, which are hereby incorporated by referenced as though fully disclosed herein.

While electrode spacing along a length of a basket's splines may be constant, a clinician may adjust the relative distance between electrodes on adjacent splines. As the relative motion of the splines is known, the distance between the electrodes on adjacent splines may also be determined. As the electrode spacing between bipole pairs in both lateral and longitudinal directions is known, advanced algorithms such as OIS/OT may be applied to signals received from adjustable basket catheters in accordance with the present disclosure. Similarly, in a planar array, in accordance with the present disclosure, the electrode spacing along the struts are constant and known, but the clinician may adjust the distance between electrodes across the struts.

In some specific aspects of the present disclosure a basket catheter including 8 splines is disclosed. Each of the splines is comprised of a shape memory material which returns to a semi-circular shape upon exiting an introducer. Each of the splines, in a first configuration, are equally distributed circumferentially about the basket relative to the other splines. When expanded, the 8 splines form a substantially spherical-shaped basket. Each of the splines include a row of electrodes extending along a length of the splines. The electrodes may be evenly distributed along the length of the splines, or unevenly distributed along the length of the splines for specialized applications. For example, the distribution of the electrodes may be weighted toward a distal end of the basket where the basket catheter is intended, for example, to diagnose cardiac arrhythmias. Many cardiac arrhythmias are triggered by stray electrical signals emanating from one or more of the pulmonary veins. Presuming a transseptal approach to the left atrium, the distal end of the basket, including its high-density of electrodes, would be orientated with the pulmonary veins.

In some specific aspects of the present disclosure, a planar array catheter including 5 struts is disclosed. Each of the struts may be aligned with, and extend parallel to, a longitudinal axis of the catheter shaft. Each strut is coupled to the other struts of the planar array at proximal and distal ends. The struts each include a row of electrodes extending along a length of the struts. The electrodes are evenly distributed along the length of the struts and between adjacent struts of the planar array. In some specific embodiments of an electrophysiology planar array catheter in accordance with the present disclosure, the planar array may include 8 struts, each strut having 8 electrodes extending along a length of the struts with 2 millimeter ("mm") spacing. The spacing between electrodes on adjacent struts also being 2 mm. However, lateral actuation of one or more of the struts along a longitudinal axis of the catheter shaft will increase the electrode spacing in a low-density electrode array region configuration to 4 mm and decrease the electrode spacing in a high-density electrode array configuration to 1 mm.

Known spacing between adjacent electrodes in an array (in two or more directions) facilitates simplified and robust OIS/OT-like assessments of orientation-specific electrical characteristics of myocardial tissue, for example. In some embodiments, known spacing directly permits 2-directional assessments of electrical activation direction and maximum voltage amplitude of sampled tissue. Moreover, known electrode spacing allows for the use of diagonal bipole pairs. Two diagonal bipole pairs, which are orthogonal relative to each other, measure the electrical characteristics of the same tissue region. The variation in readings between the orthogonal bipole pairs may be attributed to orientation-specific electrical characteristics of the contacted tissue. Embodiments of the present disclosure may further facilitate reduced complexity decimation by skipping intermediate electrodes, and forming bipole pairs with larger electrode spacing configurations than created by adjacent electrodes in the array. Decimation may be used to determine electrical characteristics of tissue at a less granular resolution. Further, a clinician may assess situational performance of the planar array at various bipole spacings. In various embodiments, consistent with the present disclosure, adjacent bipole pairs may have various spacings, and be oriented in such a way as to facilitate various spatial orientations relative to one another. Decimation may be used in conjunction with, or independent of, mechanical adjustment of the intra-electrode spacing across splines/struts, as disclosed herein.

The benefits of known electrode spacing along two or more perpendicular directions include a simplified computation of the electric field vector based only on average bipole voltages in the x, y directions. Known electrode spacing may also facilitate OIS/OT-like methods that generate bipolar electrogram signals at various orientations with respect to wavefronts, so that a clinician may employ arbitrary catheter orientations. Finally, the known electrode spacing of the array facilitates a balanced and integrated view of voltage, fractionation, and/or activation patterns, which may be readily sampled from adjacent electrodes with known spacing. This information may then be used to compute a divergence and curl (i.e., to detect/locate foci and rotor cores from activation directions).

The electrodes disclosed herein may be ring electrodes, and/or printed (spot) electrodes on substrates (e.g., flexible circuit boards). Advantageously, printed electrodes may be spaced more closely than ring electrodes. In some embodiments, for example, printed electrodes spaced 0.1 mm apart may be deployed in a planar array catheter. More typically, ring electrodes and printed electrodes may be spaced 0.5 mm to 4 mm apart. It has been found that such electrode spacing facilitates desirable electrophysiology mapping granularity in a number of cardiovascular applications, for example.

Short interelectrode spacing (e.g., 2 mm×2 mm) may be desirable to sample electrical characteristics of tissue (e.g., voltages) indicative of ablation line gaps. In testing, embodiments of the present disclosure, with short interelectrode spacings within the electrode array, detected ablation line gaps via the sampling of low voltage paths between lesions only separated by a few millimeters. Prior art electrophysiology mapping arrays, which lack the high-density electrode array (and OIS/OT algorithm-based electrogram signal processing of the present disclosure), are not capable of detecting such minute ablation line gaps.

Aspects of the present disclosure are directed toward planar array catheters and basket catheters for electrophysiology mapping. More specifically, many embodiments of the present disclosure utilize printed circuit boards (e.g., flexible printed circuit boards) to (partially) form the planar array struts and/or basket splines. Further, aspects of the present disclosure include a plurality of electrodes positioned along the planar array struts and/or basket splines. In such embodiments, the planar array struts and/or basket splines may have electrodes conductively coupled to the flexible circuit board(s). The independently addressable electrodes facilitate electrophysiology measurements of tissue, in contact with the electrodes. In many embodiments, processing circuitry samples bipole pairs of electrodes, which are orthogonal relative to one another, to determine orientation independent electrical characteristics of the tissue. It is desirable for the distance between bipole pairs of electrodes to be known to facilitate enhanced electrogram fidelity. This known positioning of electrodes on a flexible circuit board may be accomplished by existing circuit board assembly techniques (e.g., surface mount technology component placement systems, commonly referred to as "pick-and-place" machines and circuit board printing techniques). Moreover, adjustability of the planar array struts and/or basket splines relative to one another must be controllable in such a manner that known spatial positioning of the electrodes across struts/splines is known.

Conventional mapping catheter designs employ bipole electrode configurations to detect, measure, and display electrical signals from the heart. However, such conventional mapping catheter designs may be prone to error associated with the orientation of the bipole electrode pairs relative to an electrical wavefront of the heart, and result in displayed signals and mapping results that may be orientation dependent, and may not actually reflect the true (or desired) tissue properties. To mitigate this risk, aspects of the present disclosure are directed to signal processing techniques which may sample a plurality of bipole electrode pair configurations, with varying orientations, to produce accurate electrophysiology mapping results. To facilitate such signal processing techniques, electrophysiology mapping catheters consistent with the present disclosure (e.g., planar array, and basket) may utilize bipole pairs of electrodes with known spacings and varying orientations.

Bipole pair arrangements, such as those aligned with an activation direction of the electrical signals within the heart, show large amplitude signals reflecting depolarization traveling through normal or near normal tissue in contact with the bipole electrodes. Other alignments of the bipole pairs, for example, where the bipole pairs are aligned perpendicular to an activation direction of the electrical signals, or near scar tissue, may show lower amplitude fractionated signals. Various aspects of the present disclosure are directed to OIS/OT-like signal processing algorithms which separate signal amplitude and signal directionality despite poorly controlled catheter-wavefront orientation of the catheter.

For example, a first bipole pair of electrodes samples an electrical signal passing through the contact tissue in an x-orientation, and a second bipole pair of electrodes samples a second electrical signal passing through the contact tissue in a y-orientation. Signal processing circuitry may then be used to determine the true electrical signal for that location. The two bipole pairs, though substantially in the same location and in contact with the same tissue volume, may sample different electrical characteristics of the tissue due to the directionality of the electrical activation wavefronts traveling through the heart. For example, the electrical activation wavefronts that typically emanate from a sinoatrial node, and atrioventricular node. However, interfering electrical signals may also emanate from one or more of the pulmonary veins (e.g., arithmetic foci in the pulmonary vein(s)).

Importantly, to facilitate determination of important electrical characteristics of the tissue, the distance between a first bipole pair and the distance between a second bipole pair must be known.

The use of high-density electrode arrays, disclosed herein, facilitates the sampling of voltage measurements, for example, that are independent of effects associated with relative orientation of the catheter and electrical wavefront, making electrophysiology mapping of a cardiac muscle (and scar borders) much more reliable and precise. Moreover, embodiments of the present disclosure benefit from the collection of electrical signal timing information which is substantially independent from the electrode distribution. The high-density array of electrodes may also be used to verify sampled electrical signals from bipole pairs, by comparing the sampled electrical signal with other electrical signals sampled from adjacent (or nearby) bipole pairs. The regular spacing of electrodes in the high-density array further improves the accuracy of various metrics which are output from the OIS/OT algorithms and/or other signal processing techniques; for example, the En value (the estimate of the perpendicular bipole signal), an output of the Laplace equation, activation direction, conduction velocity, etc. Such aspects of the present disclosure are discussed in more detail in U.S. provisional application No. 61/944,426, filed 25 Feb. 2014, U.S. application Ser. No. 15/118,522, filed 25 Feb. 2015, and international application no. PCT/US2014/011940, filed 16 Jan. 2014, which are hereby incorporated by referenced as though fully disclosed herein.

Details of the various embodiments of the present disclosure are described below with specific reference to the figures.

Figure 1B:
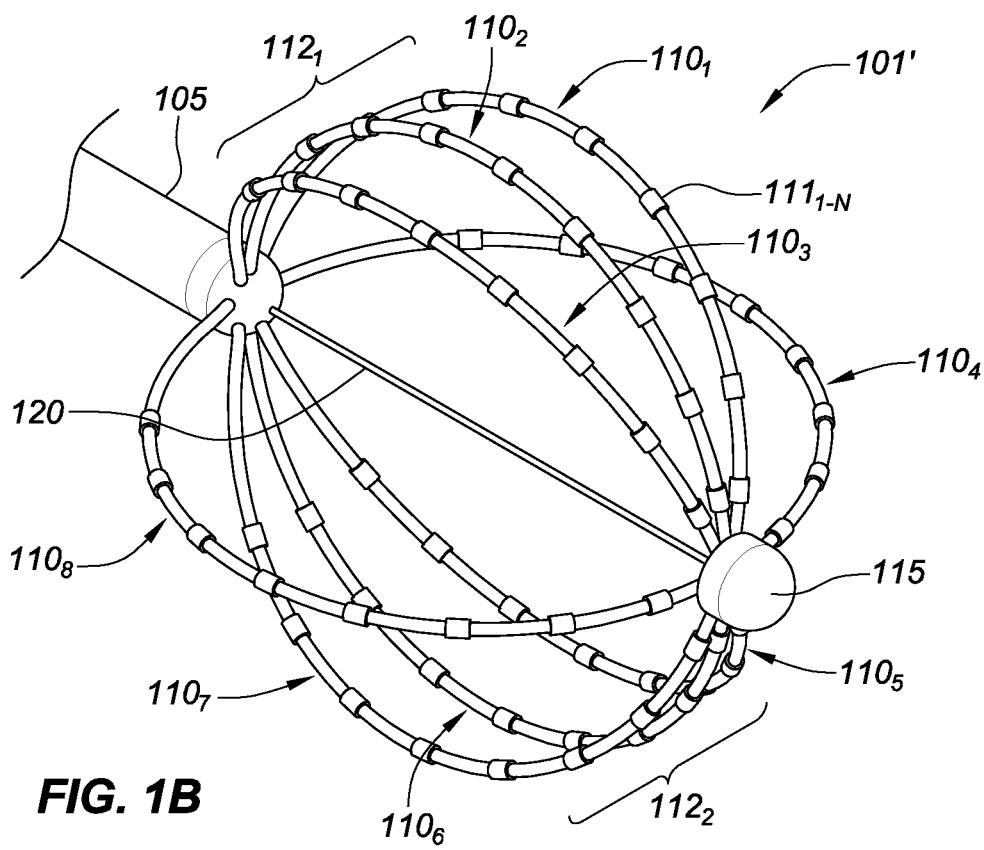
FIG. 1B is an isometric side view of the basket end effector of FIG. 1A with a number of the basket splines re-positioned to facilitate a more concentrated electrode array for regional mapping, consistent with various embodiments of the present disclosure.

FIG. 1A is an isometric side view of a basket end effector 101 (also referred to as a basket catheter) of an electrophysiology catheter configured for global mapping, and FIG. 1B is an isometric side view of the basket end effector 101 of FIG. 1A with a number of the basket splines $110_{1-8}$ repositioned to form a high-density array region for regional mapping, consistent with various embodiments of the present disclosure.

The basket catheter 101 of FIG. 1A is shown in an expanded configuration. The basket 101 is comprised of a plurality of splines $110_{1-8}$ which are coupled to a catheter shaft 105 at a proximal end and to a distal cap 115 (or one another) at a distal end. While the present embodiment presents a basket comprised of eight splines $110_{1-8}$, basket catheters with three or more splines are readily envisioned, with the design depending on an intended clinical application and desired electrophysiology mapping granularity. To facilitate expansion/contraction of the basket, a deployment member 120 extends along a longitudinal axis of the basket. The deployment member 120 in some embodiments may be a pull-wire which extends between a catheter handle and a distal cap 115. Actuation of the pull-wire causes expansion/contraction of the basket. In other embodiments, the deployment member 120 may be a lumen which is actuated by a manipulator on the catheter handle to expand/contract the basket. In yet further embodiments, the splines $110_{1-8}$ may be comprised of a shape-memory alloy (e.g., nitinol) which returns to a semi-circular shape after exiting an introducer, negating the need for a deployment member 120.

In the present embodiment, each of the splines $110_{1-8}$ includes a plurality of electrodes $111_{1-N}$ distributed about a length of each spline. While the embodiment presented in FIGS. 1A-G depicts electrode $111_{1-N}$ regularly distributed along the length of each spline, other embodiments may include unevenly distributed electrodes along the splines. For example, in pulmonary vein electrophysiology mapping applications, only a distal portion of the basket may be in contact with tissue proximal the pulmonary veins. Accordingly, a distribution of electrodes $111_{1-N}$ may be weighted toward a distal end of the basket 101 to facilitate enhanced electrophysiology mapping granularity in proximity to the pulmonary veins.

The electrodes $111_{1-N}$ may be used in various bipole configurations to facilitate measurement of electrical characteristics of tissue in contact with the electrodes. Orthogonally-oriented bipole pair combinations are capable of measuring the unique orientation specific electrical characteristics of the tissue in two orthogonal orientations. A first bipole pair may include a pair of electrodes 111 along a length of a spline 110, facilitating the collection of tissue electrical characteristic data in an orientation substantially parallel with the catheter's longitudinal axis. A second, orthogonal bipole pair may extend laterally across adjacent splines 110, facilitating the collection of tissue electrical characteristic data in an orientation substantially transverse to the catheter's longitudinal axis. To facilitate collecting this electrical data, these bipole electrode pairs may be independently addressable by signal processing circuitry. The signal processing circuitry analyzes the received signals from the two sets of bipole pairs to determine orientation independent electrophysiology information of the tissue in contact with the electrodes.

In various embodiments consistent with the present disclosure, the splines 110 may be formed from flexible electronic circuit boards with each of the electrodes 111 coupled thereto and communicatively coupled to signal processing circuitry via electrical traces that extend along interior or exterior layers of the flexible printed circuit board. In some specific embodiments, each of the splines 110 may consist of nitinol. In such embodiments, the flex circuit may be either bonded directly to the nitinol, or, alternatively, the flex circuit may be directly bonded to pebax tubing which houses the nitinol spline internally.

In some embodiments, the electrodes 111 may be 0.8 millimeters in diameter with a total surface area of 0.5 mm$^2$. The electrodes 111 on the basket catheter 101 need not be uniform in size and shape. For example, embodiments consistent with the present disclosure may include smaller size electrode(s) (e.g., 0.8 mm in diameter) for electrophysiology mapping, and larger size electrode(s) that may be capable of both electrophysiology mapping and have a large enough impedance to facilitate localization in an impedance or hybrid-based catheter navigation system (e.g., MediGuide™ System, and/or EnSite NavX™ system). In one particular embodiment, the smaller electrophysiology mapping electrodes may be coupled to an external-facing surface of the splines for direct contact with tissue, with larger, non-contact navigation electrodes coupled to an internal-facing surface of the splines 110.

While it may be desirable in some embodiments to have equal spacing between all of the electrodes 111 both on a spline 110 and between splines, knowledge of the relative spacing between each of the electrodes which form bipole pairs is sufficient to accurately capture orientation-specific electrical characteristic data of tissue in contact with the electrodes. In some specific embodiments, an edge-to-edge spacing for one or more of the bipole pairs of electrodes may be between 2-2.5 millimeters. In yet other specific embodiments, center-to-center spacing of the electrodes in a bipole pair may be between 0.5-4 millimeters.

In some specific embodiments, some of the electrodes 111 on the basket 101 may be multi-purpose, while other electrodes are single-purpose. For example, some of the electrodes may function as both navigation and electrophysiology mapping electrodes, others may function only as electrophysiology mapping electrodes, and yet other electrodes may function only as navigation electrodes.

As shown in FIG. 1B, four splines $110_{1,3,5,7}$ are rotated relative to the remaining four splines $110_{2,4,6,8}$ to create high-density array regions $112_{1-2}$. The high-density array regions may be used for regional mapping of areas of interest. Global mapping of a cardiac chamber, for example, is often followed by regional mapping using another catheter. The present basket catheter 101' is capable of performing both global and regional mapping operations by adjusting the electrode array density in the high-density array regions $112_{1-2}$. Actuation of the moveable splines $110_{1,3,5,7}$ may be accomplished via a clinician's input on a catheter handle. Upon completion of a regional electrophysiology mapping, the moveable splines $110_{1,3,5,7}$ may be returned to evenly circumferentially distributed positions for global mapping (as shown in FIG. 1A). In various embodiments of the present disclosure, one or more of the splines 110 may be rotatably adjusted to facilitate more or less electrode array density. Moreover, in some embodiments matched splines opposite one another (e.g., splines $110_{2,6}$) may be independently adjustable, or in other implementations may be dependent and actuated simultaneously.

Figure 1C:
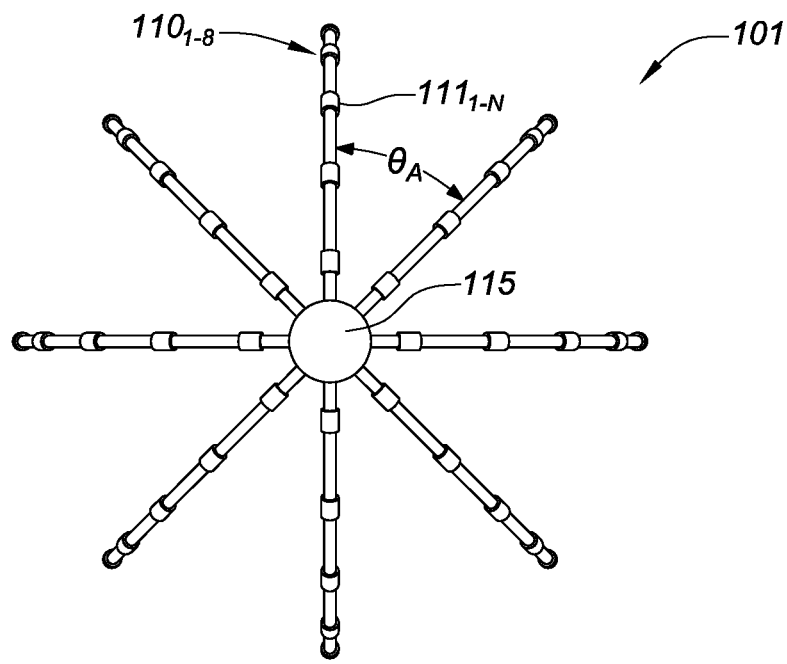
FIG. 1C is an end view of the basket end effector of FIG. 1A, consistent with various embodiments of the present disclosure.

FIG. 1C is an end view of the basket catheter 101 of FIG. 1A, consistent with various embodiments of the present disclosure. As shown in FIG. 1A, each basket spline $110_{1-8}$ is rotationally offset from the adjacent splines by approximately $\theta_A$. In the present embodiment, equal spacing of each of the eight splines 110 results in an offset, $\theta_A$, between the splines of approximately 45°. The basket catheter 101 may take such a configuration in order to conduct a global electrophysiology mapping of a region (e.g., cardiac chamber). In FIG. 1A, the known angle between the splines 110 further facilitates a known distance relationship between electrodes 111$_{1-N}$. In various embodiments, electrode bipole pairs may extend between adjacent splines 110, and the known distance therebetween may be used to determine various electrical characteristics of the tissue in contact with the bipole pair.

As further shown in FIG. 1C, a distal cap 115 may serve several purposes including coupling distal ends of the splines 110$_{1-8}$ back to one another (near a longitudinal axis of the catheter), and providing a distal most surface of the catheter that prevents unintentional trauma to tissue contacted therewith.

Figure 1D:
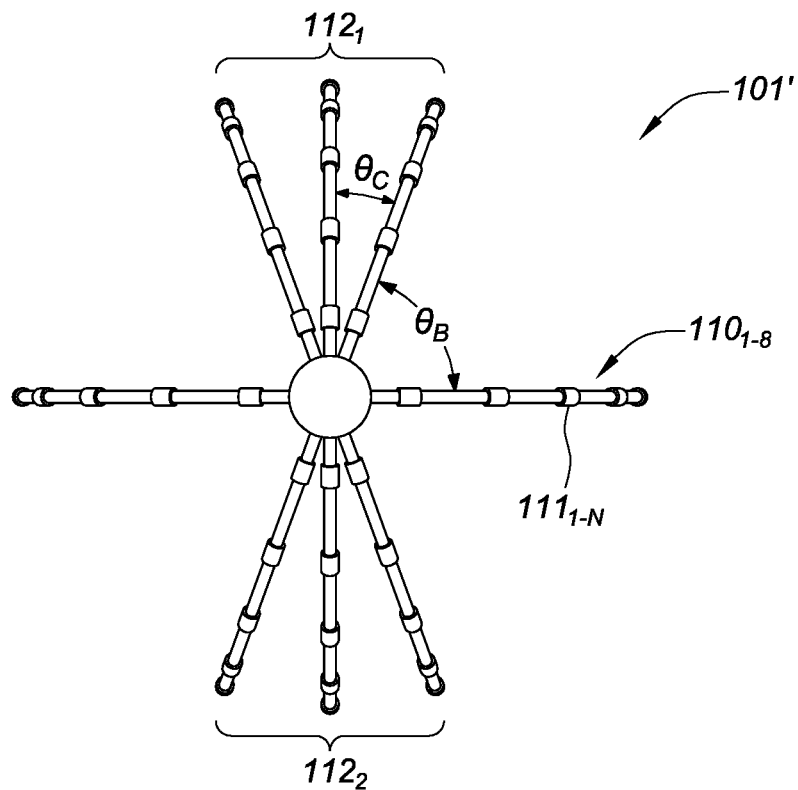
FIG. 1D is an end view of the basket end effector of FIG. 1B, consistent with various embodiments of the present disclosure.

FIG. 1D is an end view of the basket catheter 101' in the configuration shown in FIG. 1B. As shown in FIG. 1D, one or more of the splines 110$_{1-8}$ have been actuated to create high-density array regions 112$_{1-2}$ which facilitate use of the basket catheter 101' as a regional electrophysiology mapping device (as well as a global electrophysiology mapping device as shown in FIGS. 1A and 1C). The high-density array regions 112$_{1-2}$ exhibit angle, $\theta_C$, between splines of approximately 30°, in one example. Where even further mapping granularity for the high-density array regions 112$_{1-2}$ is desired, the angle, $\theta_C$, between the splines may be further decreased. In some specific embodiments, it may be desirable to achieve distances between electrodes 111$_{1-N}$ on adjacent splines of 0.5 millimeters, or less. Where the regional mapping configuration of the basket catheter 101' includes splines 110 outside of the high-density array regions 112$_{1-2}$, the angle, $\theta_B$, between such splines may be, for example, approximately 60°. In some embodiments, all of the splines may be actuated into the one or more high-density array regions 112$_{1-2}$. While the present embodiment shows two high-density array regions 112$_{1-2}$, in some more specific embodiments, where even further mapping granularity is desired, all of the splines may be configured into a single high-density array region.

Figure 1E:
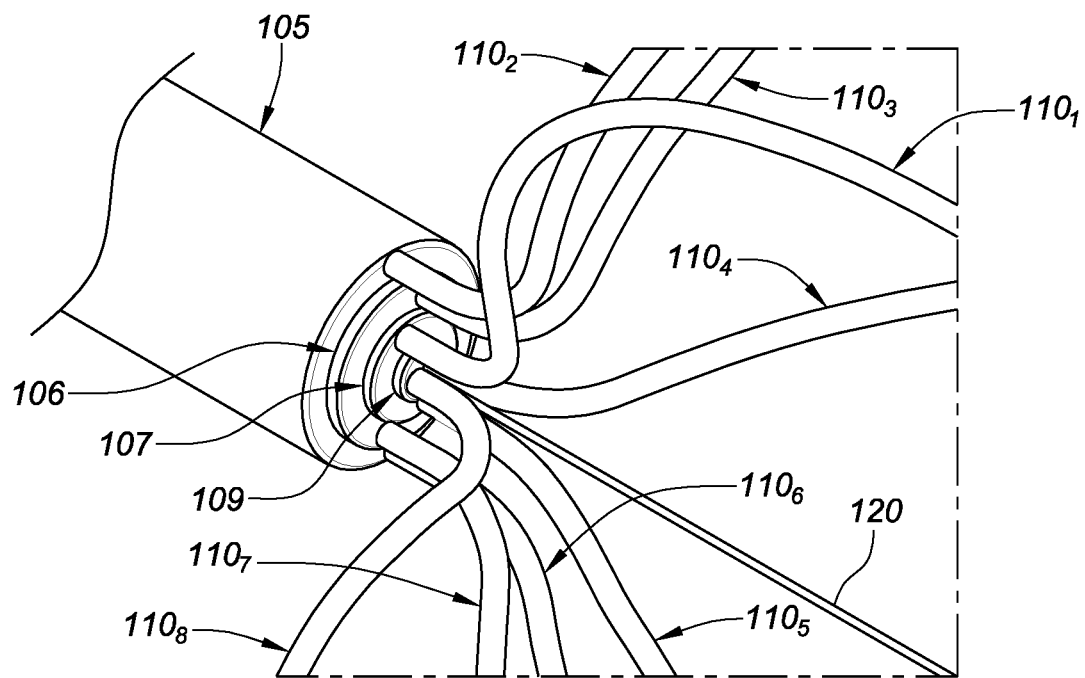
FIG. 1E is a close-up, isometric side view of a proximal portion of the basket end effector of FIG. 1B, consistent with various embodiments of the present disclosure.

FIG. 1E is a close-up, isometric side view of a proximal portion of basket catheter 100 of FIG. 1A. As shown in FIG. 1E, rotational actuation of one or more of splines 110$_{1-8}$ may be accomplished, for example, by rotating one or more shafts 105, 106, 107, and 109. The shafts may extend a length of the catheter and may be coupled to controls on a catheter handle. In some embodiments, one or more splines 110$_{1-8}$ may be static, while other splines may be rotatably actuated. For example, catheter shaft 105 and inner shaft 109 may be statically coupled to a catheter handle. Accordingly, splines 110$_{2,4,6,8}$ maintain a relative angular configuration relative to the catheter assembly, and may not be rotated without rotating the entire assembly. In other embodiments, one or both of catheter shaft 105 and inner shaft 109 may be rotatably actuated facilitating the adjustment of splines 110$_{2,4,6,8}$. A first intermediate shaft 106 coupled to splines 110$_{3,7}$, and second intermediate shaft 107 coupled to splines 110$_{1,5}$ may be rotatably actuated by a clinician at the catheter handle. Accordingly, a clinician during a therapy and/or diagnostic procedure using the basket catheter may independently adjust an angular position of splines 110$_{1,3,5,7}$ (and in some embodiments splines 110$_{2,4,6,8}$). By independently adjusting the angular position of the splines relative to one another, a clinician may modify the resolution of an electrophysiology map. For example, after conducting an initial global electrophysiology mapping of a cardiac chamber, a clinician may further refine the resolution of the electrophysiology map in a region of interest by moving additional splines into the interest region (see, e.g., FIG. 1B).

In some embodiments, the adjustment of each of the splines 110$_{1-8}$ may be independent of the others. As shown in FIG. 1E, pairs of splines (e.g., splines 110$_{2 \text{ and } 6}$, splines 110$_{3 \text{ and } 7}$, splines 110$_{1 \text{ and } 5}$, and splines 110$_{4 \text{ and } 8}$) are rotatably dependent upon one another as the pairs are coupled to the same shafts 105, 106, 107, and 109. Moreover, while some embodiments are directed to catheter handles with individual actuation mechanisms for each of the shafts which are independently adjustable, more specific embodiments, may utilize a single, multi-stage actuation mechanism for all of the adjustable splines 110 (see, e.g., FIG. 1G).

While some embodiments may include splines 110 formed of shape-memory alloys, for example, which facilitate automatic deployment of the basket catheter upon exit of the basket from an introducer, the embodiment of FIGS. 1A-G includes a deployment member 120 (e.g., pull-wire) coupled to a distal cap and extends proximally to a catheter handle at a proximal end of the catheter shaft 105. Actuation of the pull-wire results in the expansion/contraction of the basket. In other embodiments, the deployment member 120 may be a lumen which may be actuated by a manipulator on the catheter handle to expand/contract the basket. The deployment member 120 may extend through a lumen in inner shaft 109.

Figure 1F:
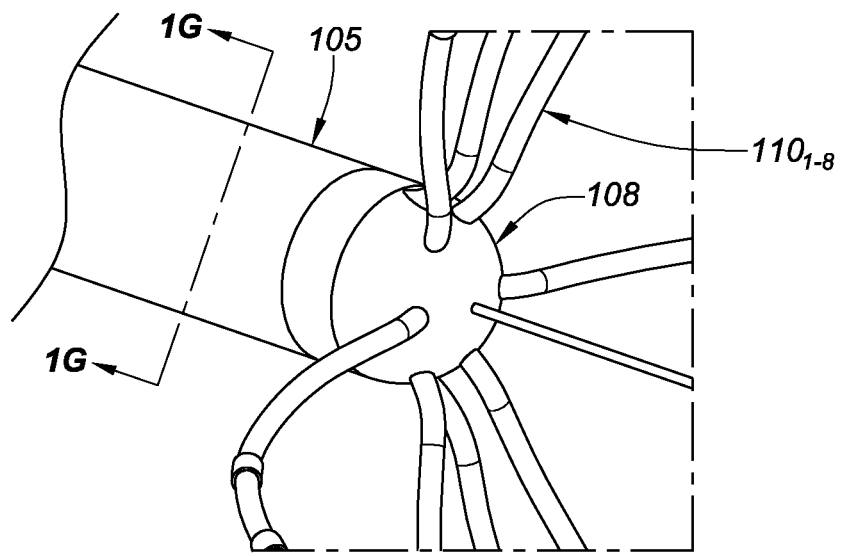
FIG. 1F is a close-up, isometric side view of a proximal portion of the basket end effector of FIG. 1B, consistent with various embodiments of the present disclosure.

FIG. 1F is a close-up, isometric side view of a proximal portion of a basket catheter in a second configuration 101' as shown in FIG. 1B. As shown in FIG. 1F, an elastomeric cap 108 map be overmolded (or otherwise coupled) to distal ends of shafts 105, 106, 107, and 109, and partially encapsulate proximal portions of splines 110$_{1-8}$. The elastomeric cap 108 facilitates relative motion of the splines 110 while also sealing the interstitial spaces between the shafts from bodily fluids. Importantly, the elastomeric cap 108 facilitates the return of the splines to a home position after clinician actuation is discontinued. The home position may be, for example, a global mapping configuration, a regional mapping configuration, or some configuration there between.

Figure 1G:
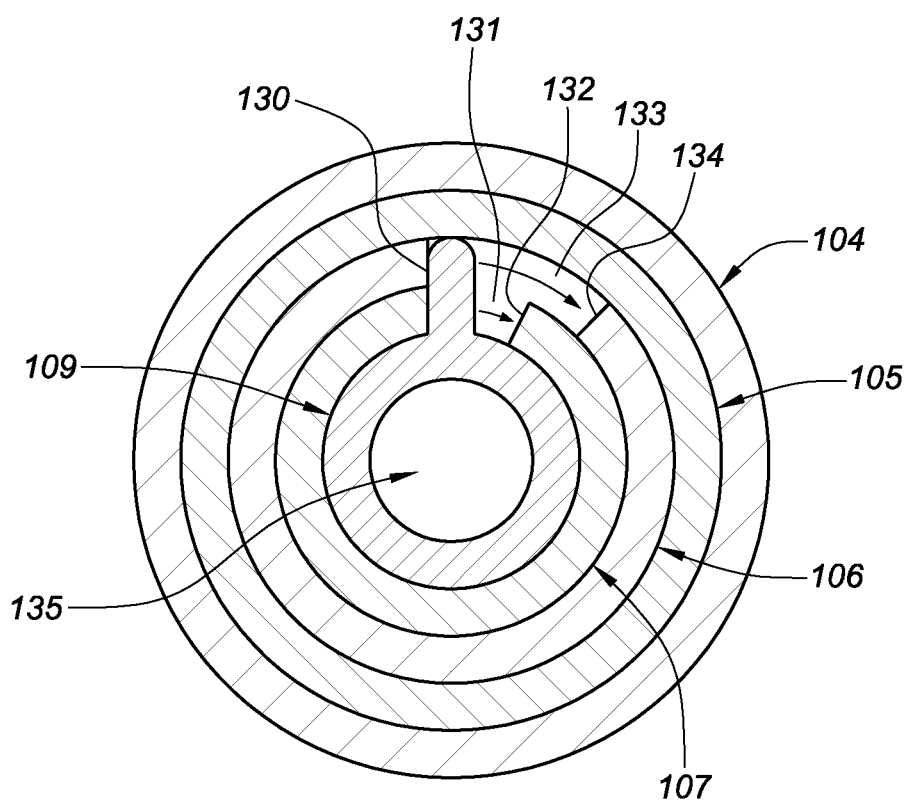
FIG. 1G is a cross-sectional end view of a catheter shaft of FIG. 1A, consistent with various embodiments of the present disclosure.

FIG. 1G is a cross-sectional end view of an outer shaft 105 of basket catheter 101, within an introducer 104. The outer shaft 105 houses first and second intermediate shafts, 106 and 107, respectively, and inner shaft 109. In some embodiments, the inner shaft 109 includes a lumen 135 for delivering wiring, irrigation, etc. between distal and proximal ends of the catheter. The outer shaft, first and second intermediate shafts, and inner shaft are all coupled to one or more splines at a distal end of the catheter.

In response to a user's actuation of a control on a catheter handle, a first rotational motion 131 of an inner shaft 109, including a first keying feature 130, occurs. When the inner shaft 109 is rotated, splines coupled to the inner shaft rotate-in-kind.

During a second rotational motion 133, which occurs after the inner shaft has completed a first rotational motion 131 (approximately 30° from a home position), first keying feature 130 contacts a second keying feature 132 of second intermediate shaft 107. The contact between the first and second keying features cause the second intermediate shaft to rotate with the inner shaft. As a result, the splines coupled to both the inner shaft and second intermediate shaft splines rotate together during the second rotational motion 133. After a total of approximately 60° of motion, the first keying feature 130 contacts a stop 134 on first intermediate shaft 106, which prevents any further rotational motion of the inner shaft and second intermediate shaft. In the present embodiment, the splines on both outer shaft 105 and first intermediate shaft 106, and the shafts themselves, do not rotate. Accordingly, the rotation of the splines coupled to inner shaft 109 and second intermediate shaft 107 facilitates the reconfiguration of the basket catheter between a regional and global electrophysiology mapping configuration.

Figure 2A:
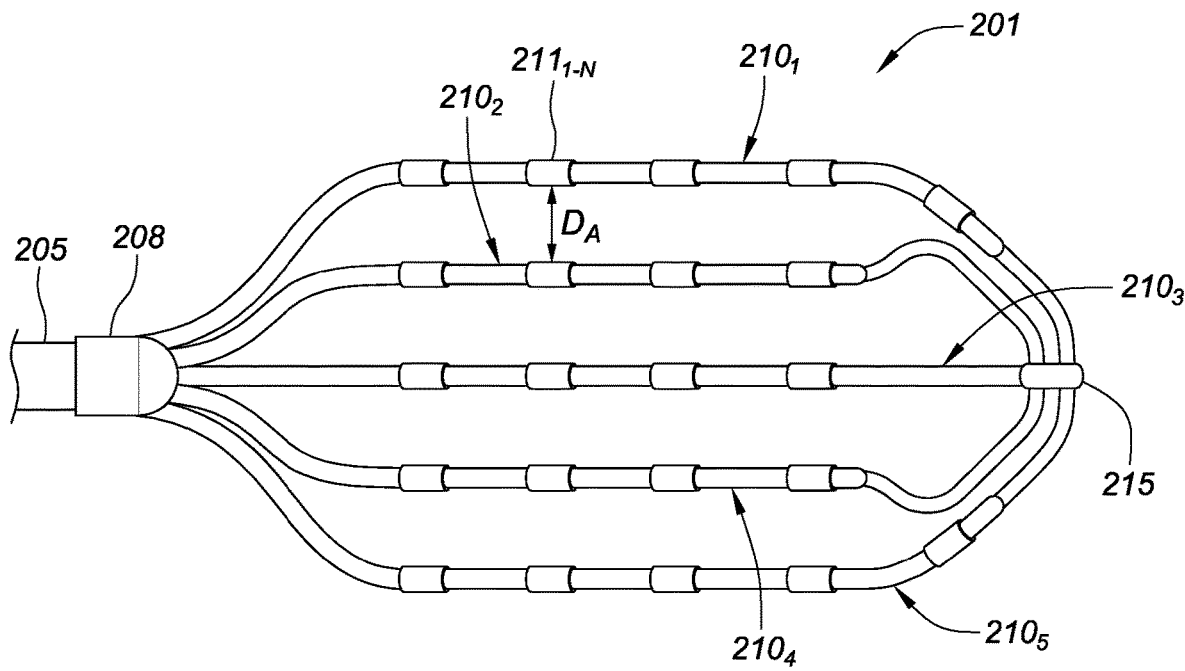
FIG. 2A is an isometric, top view of a planar end effector of an electrophysiology mapping catheter configured for regional mapping, consistent with various embodiments of the present disclosure.
Figure 2B:
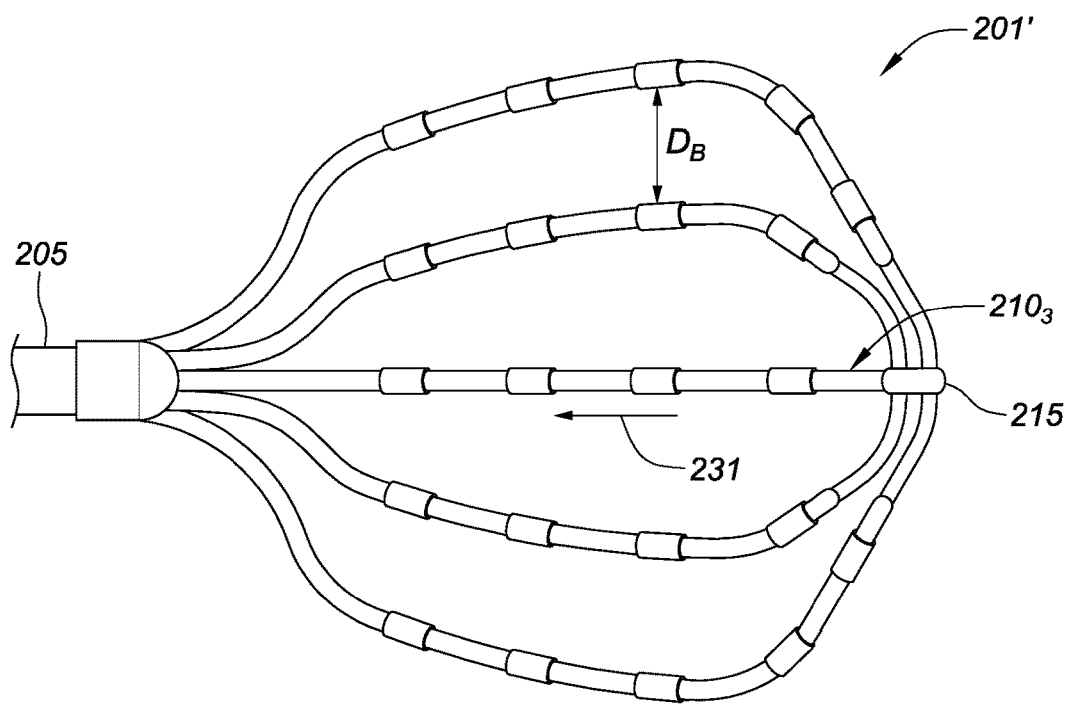
FIG. 2B is an isometric, top view of the planar end effector of FIG. 2A with the splines laterally extended to conduct global mapping, consistent with various embodiments of the present disclosure.

FIG. 2A is an isometric, top view of a planar end effector 201, of an electrophysiology mapping catheter configured for regional mapping (a first configuration), and FIG. 2B is an isometric, top view of the planar end effector 201' of FIG. 2A, in a second configuration. As shown in FIG. 2B, the splines are laterally extended to conduct global mapping, consistent with various embodiments of the present disclosure.

The planar array 201 of an electrophysiology mapping catheter includes a high-density array of electrodes $211_{1-N}$, consistent with various embodiments of the present disclosure. The planar array 201 forms a flexible array of the electrodes $211_{1-N}$. This array of electrodes is coupled to a flexible framework of struts $210_{1-5}$ which extend in a plane that is substantially parallel with a longitudinal axis of catheter shaft 205. Each of the struts is precisely, laterally separated from each other to facilitate exact spacing between electrodes $211_{1-N}$ on adjacent struts $210_{1-5}$, and the struts are coupled to one another at distal and proximal ends (e.g., at a distal tip 215 and bushing 208).

As shown in FIG. 2A, each of the five struts $210_{1-5}$ may carry a plurality of electrodes 211 with the spacing of the electrodes along a length of the strut being the same (or at least known). Similarly, the spacing between electrodes 211 across struts 210 of the array may also be equal (or at least known). The result is a plurality of electrode bipole pairs with known spacings. For example, in some embodiments the center-to-center electrode spacing of a bipole pair may be between 0.5-4 mm. In yet more specific embodiments, the center-to-center electrode spacing of a bipole pair may be less than 0.5 millimeters (e.g., 0.1 mm). While the present embodiment is directed to bipole pairs with equal center-to-center spacing, various other embodiments of an electrode array, consistent with the present disclosure, may include an electrode array with equal edge-to-edge spacing. For example, in some embodiments the edge-to-edge electrode spacing may be between 0.5-4 mm. In yet more specific embodiments, the edge-to-edge electrode spacing may be less than 0.5 millimeters (e.g., 0.1 mm). Consideration of edge-to-edge spacing may be desirable where the electrodes 211 of the array 201 have different relative sizes (or surface areas).

Although the planar array 201 in FIG. 2A depicts five struts $210_{1-5}$, the catheter may comprise more or less struts, with spacing between each respective strut based on a desired electrode spacing for a given electrophysiology application. Additionally, while the planar array 201 depicted in FIG. 2A shows 22 electrodes 211, the planar array may include more or fewer than 22 electrodes, and each strut need not have the same number of electrodes as adjacent struts.

In some embodiments, the electrodes $211_{1-N}$ may be used in diagnostic, therapeutic, and/or mapping procedures. For example and without limitation, the electrodes 211 may be used for electrophysiological studies, pacing, cardiac mapping, and ablation. In some embodiments, the electrodes 211 may perform unipolar or bipolar ablation (e.g., via the use of bipole pairs of electrodes). This unipolar or bipolar ablation may create specific lines or patterns of lesions. In some embodiments, the electrodes 211 may receive electrical signals from the heart, which can be used for electrophysiological studies/mapping. Importantly, as the electrode spacing between adjacent electrodes on a strut 210, and those on adjacent struts, are the same (or otherwise known), bipole pairs with varying relative orientations may be sampled to determine electrical characteristics of the tissue in contact with the bipole pairs. The sampled electrical characteristics may be processed to remove catheter orientation-based signal effects. In some embodiments, the electrodes 211 may perform a location or position sensing function related to cardiac mapping (e.g., determine location and/or orientation of the catheter 201).

The planar array 201 is coupled to a distal end of a catheter shaft 205 at a bushing 208 (also referred to as a connector). The catheter shaft 205 may also define a catheter shaft longitudinal axis. In the present embodiment, each of the struts $210_{1-5}$ extend substantially parallel to the longitudinal axis. The catheter shaft 205 may be made of a flexible material, such that it can be threaded through a tortuous vasculature of a patient. In some embodiments, the catheter shaft 205 may include one or more ring electrodes disposed along a length of the catheter shaft. The ring electrodes may be used for diagnostic, therapeutic, localization and/or mapping procedures, for example. In one embodiment, planar array 201 may include a magnetic field sensor configured for use with an electromagnetic localization system such as the MediGuide™ System sold by St. Jude Medical, Inc. of St. Paul, Minn.

The planar array 201 may be adapted to conform to tissue (e.g., cardiac tissue). For example, when the planar array contacts tissue, each strut $210_{1-5}$ may independently deflect to conform to the tissue. The ability for the planar array to deflect in response to tissue may be particularly beneficial when the planar array comes into contact with contoured, irregular, or trabeculated tissue. In some embodiments, the struts 210 (or the understructure of the struts) may be constructed from a flexible or swing-like material such as nitinol and/or a flexible substrate. The construction of the planar array struts $210_{1-5}$ (including, for example, the length and/or diameter of the struts, and material) may be tailored to achieve desired resiliency, flexibility, foldability, conformability, and stiffness characteristics. Moreover, in some embodiments, it may be desirable to vary one or more characteristics from the proximal end of a strut to the distal end of the strut, or between or among the plurality of struts forming the planar array 201. The collapsibility of materials such as nitinol and/or a flexible substrate provides the added benefit of facilitating insertion of the planar array into a delivery sheath or introducer, whether during delivery of the catheter into the body or removal of the catheter from the body at the end of a procedure.

Planar array catheters including the high-density electrode array positioned thereon may be used for, for example: (1) defining regional propagation maps of particularly sized areas on the walls of the heart; (2) identifying complex fractionated atrial electrograms for ablation; (3) identifying localized, focal potentials between the electrodes for higher electrogram resolution; and/or (4) more precisely targeting areas for ablation. Additionally, the catheters described herein may find application in epicardial and/or endocardial use. For example, the planar array embodiments depicted herein may be used in epicardial procedures where the planar array of electrodes is positioned between the myocardial surface and the pericardium. Alternatively, the planar array embodiments may be used in an endocardial procedure to sweep and/or analyze the inner surfaces of the myocardium and create high-density maps of the heart tissue's electrical properties.

While various embodiments of the planar array 201 disclosed in the present disclosure are depicted with ring electrodes $211_{1-N}$ coupled to the struts $210_{1-5}$, embodiments with spot-type electrodes coupled to the struts are readily envisioned. Moreover, in yet further embodiments, the struts of the planar array may comprise flexible thin films compatible with printed circuit manufacturing techniques and/or have such thin films coupled to structural elements of the strut (e.g., nitinol-based structural elements). In such embodiments, spot-type electrodes may be printed onto the struts themselves. In flexible printed circuit embodiments of the present disclosure, the printed electrodes may be electrically coupled to signal processing circuitry and/or driver circuitry via traces extending on or within the one or more thin film layers. As many electrophysiology mapping applications require high signal fidelity, it is desirable to limit the transmission length of the analog signal, shield the transmission line itself, and/or convert the analog signal to a digital signal close to the source of the analog signal. Accordingly, aspects of the present disclosure are directed to placing signal processing circuitry (e.g., analog-to-digital converters, signal conditioning such as noise filtration and bandpass filters), and/or driver circuitry on the struts $210_{1-5}$ or in close proximity thereto.

In embodiments of the planar array 201 including ring electrodes $211_{1-N}$, the ring electrodes of the high-density electrode array may include the same type of electrode or a variety of various electrode types. For example, electrodes with smaller surface area may be used exclusively for electrophysiology mapping, while larger surface area electrodes may be used for mapping, tissue ablation, and/or localization. In some specific embodiments, the electrode array may include one or more slightly enlarged ring electrodes. These slightly enlarged electrodes may be used, for example, for more precise localization of the flexible array in mapping and navigation systems. It may also be possible to drive ablation current between these enlarged electrodes, if desired, for bipolar ablation, or, alternatively to drive ablation current in unipolar mode between one or more of these enlarged ring electrodes and, for example, a patch electrode located on a patient (e.g., on the patient's back). Similarly, the electrodes $211_{1-N}$ in some embodiments may all be capable of performing unipolar or bipolar ablation therapies. Alternatively or concurrently, current may travel between one or more of the enlarged electrodes and any one or all of the electrodes. This unipolar or bipolar ablation therapy technique may be used to create specific lesion lines or lesion patterns. As also seen in FIG. 2A, there may be a distal tip 215 where one or more of the struts $210_{1-5}$ come together. This distal tip 215 may be constructed from metal or some other radiopaque material to provide fluoroscopy visualization. The distal tip 215 may further facilitate (semi-) independent planar movement between the struts $210_{1-5}$.

In some embodiments of the present disclosure, the mapping catheter 201 may include steering wires which extend a length of catheter shaft 205. Prior to reaching a bushing 208 that couples the catheter shaft 205 to struts $210_{1-5}$ of planar array 201, the steering wires may be coupled to one or more steering rings which receive a force from a proximal end of the steering wires and facilitates steering the catheter shaft 205 and the planar array 201 through a patient's vasculature. As further shown in FIG. 2A, each of the struts $210_{1-5}$ includes a plurality of electrodes $211_{1-N}$ distributed along a length of the struts. In the present embodiment, each of the electrodes are equally spaced ($D_A$) from each of the adjacent electrodes. When controller circuitry samples electrical signals from bipole pairs of electrodes within the planar array 201, each of the bipole pairs will detect various electrical characteristics indicative of the tissue health in contact with the electrodes. The five struts $210_{1-5}$ are designed to maintain the electrodes $211_{1-N}$ in a spaced relationship so that each bipole pair of electrodes capture electrophysiology data of tissue across a known distance.

While many embodiments of the present disclosure are directed to electrophysiology mapping, embodiments of the present disclosure may also be configured for pacing (as well). For example, one or more electrodes $211_{1-N}$ may send pacing signals to, for example, cardiac tissue.

Though not shown in FIGS. 2A-B, various embodiments of the planar array catheter 201 may include one or more irrigation ports. For example, proximal irrigant port(s) may be located on/at the distal end of proximal bushing 208, the proximal irrigant port(s) positioned to deliver irrigant to or near the point where the electrode carrying struts $210_{1-5}$ exit from the distal end of the proximal bushing, that is mounted on the distal end of the catheter shaft 205 in this embodiment. In some more specific embodiments, a second, distal irrigation port(s) may be located near the distal intersection of the struts $210_{1-5}$ and on or near distal tip 215. In yet further embodiments, if desired, multiple irrigation ports could be present at various positions along the struts 210. Where more than one irrigant port is positioned at proximal and/or distal ends of the planar array 201, more uniform irrigant distribution at or near the proximal/distal apex of the struts 210 may be facilitated.

As shown in a second configuration 201' of the planar array of FIG. 2B, strut $210_3$ has been actuated by a clinician in a proximal direction 231. The actuation causes lateral deflection of struts $210_{1,2,4,5}$ (via distal tip 215), which in turn changes a distance between electrodes $211_{1-N}$ on adjacent struts from $D_A$ to $D_B$ (where $D_B$ is a known distance). Of course, the distance between electrodes running along a length of the struts 210 will not change in response to the actuation. The change in electrode spacing between adjacent struts facilitates variable granularity electrophysiology mapping of target tissue. The deflection of the struts facilitates a more global mapping of target tissue, at least laterally relative to a longitudinal axis of the catheter.

Figure 3A:
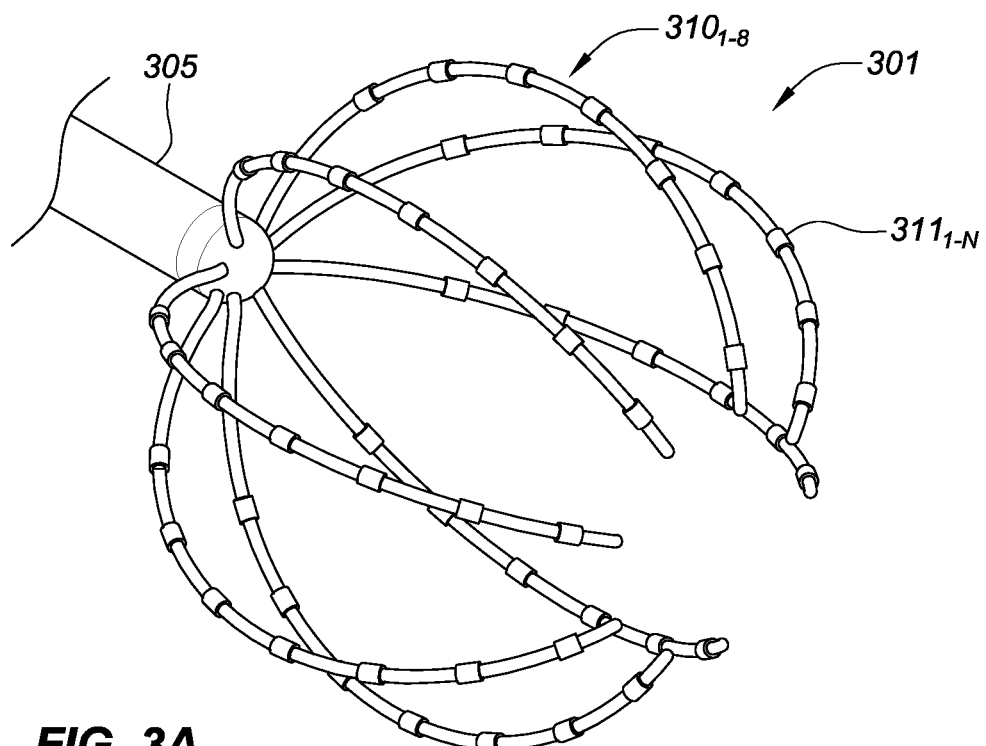
FIG. 3A is an isometric side view of a basket end effector of an electrophysiology catheter configured for global mapping, consistent with various embodiments of the present disclosure.
Figure 3B:
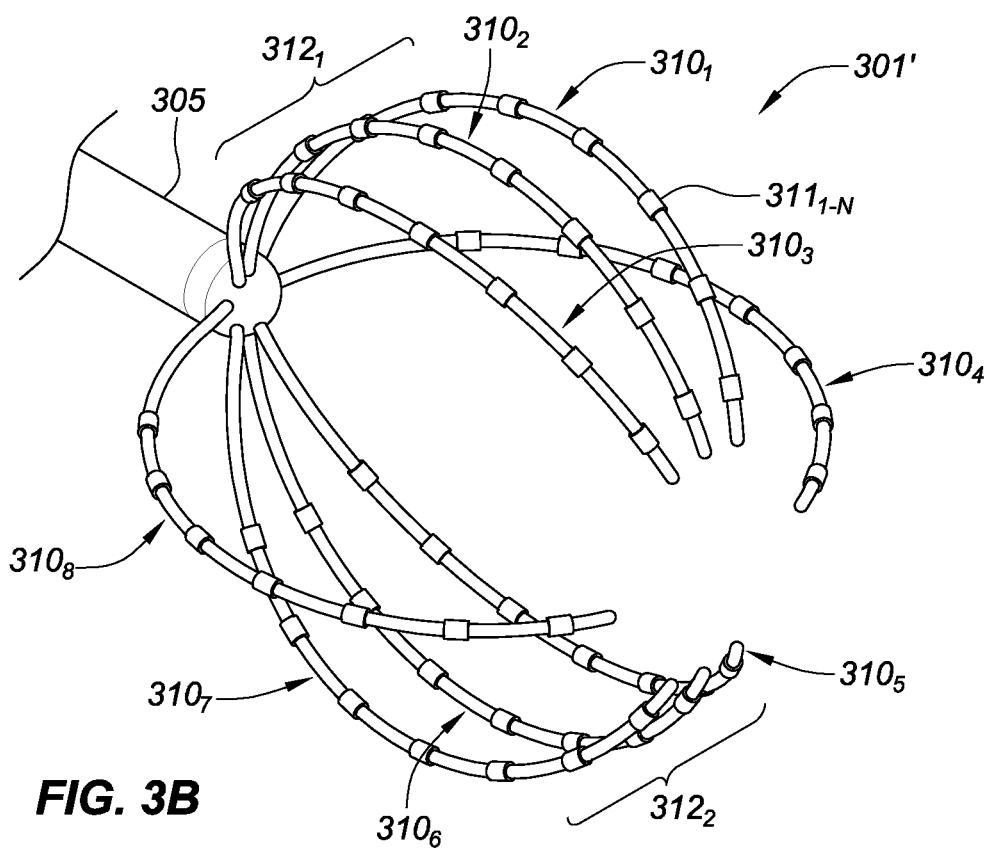
FIG. 3B is an isometric side view of the basket end effector of FIG. 3A with a number of the basket splines re-positioned to facilitate a more concentrated electrode array for regional mapping, consistent with various embodiments of the present disclosure.

FIG. 3A is an isometric side view of a basket end effector 301 of an electrophysiology catheter configured for global mapping, and FIG. 3B is an isometric side view of the basket end effector 301 of FIG. 3A with a number of basket splines $310_{1-8}$ re-positioned into a second configuration 301' to form one or more high-density array region(s) for regional mapping.

The basket end effector 301 of FIG. 3A is shown in an expanded configuration. The basket end effector 301 is comprised of a plurality of splines $310_{1-8}$ which are coupled to a catheter shaft 305 at a proximal end and free at a distal end. While the present embodiment presents a basket comprised of eight splines $310_{1-8}$, basket catheters with three or more splines are readily envisioned. The design may depend on an intended clinical application and desired electrophysiology mapping granularity. To facilitate expansion/contraction of the basket, the splines $310_{1-8}$ may be comprised of a shape-memory alloy (e.g., nitinol) which returns to a semicircular shape after exiting an introducer. In yet other embodiments, each of the splines may be coupled to one or more steering wires which when actuated expand and/or contract the splines to form the desired shape.

In FIG. 3A, each of the splines $310_{1-8}$ include a plurality of electrodes $311_{1-N}$ distributed about a length of the spline. The electrodes $311_{1-N}$ may be used in various bipole configurations to facilitate measurement of electrical characteristics of tissue in contact with the electrodes. Orthogonally-oriented bipole pair combinations may be used to measure the unique orientation specific electrical characteristics of the tissue in two orthogonal orientations. A first bipole pair may include a pair of electrodes 311 along a length of a spline 310, facilitating the collection of tissue electrical characteristic data in an orientation substantially parallel with the catheter's longitudinal axis. A second, orthogonal bipole pair may extend laterally across adjacent splines 310, facilitating the collection of tissue electrical characteristic data in an orientation substantially transverse to the catheter's longitudinal axis. To facilitate collecting this electrical data, these bipole electrode pairs may be independently addressable by signal processing circuitry. The signal processing circuitry analyzes the received signals from the two sets of bipole pairs to determine orientation independent electrophysiology information of the tissue in contact with the electrodes.

In various embodiments consistent with the present disclosure, the splines 310 may be formed from flexible electronic circuit boards with each of the electrodes 311 coupled thereto and communicatively coupled to signal processing circuitry via electrical traces that extend along interior or exterior layers of the flexible printed circuit board. In some specific embodiments, each of the splines 310 may consist of nitinol. In such embodiments, the flex circuit may be either bonded directly to the nitinol, or, alternatively, the flex circuit may be directly bonded to pebax tubing which houses the nitinol spline internally.

While it may be desirable in some embodiments to have equal spacing between all of the electrodes 311 both on a spline 310 and between splines, knowledge of the relative spacing between each of the electrodes which form bipole pairs is sufficient to accurately capture orientation-specific, electrical characteristic data of tissue in contact with the electrodes.

In some specific embodiments, some of the electrodes 311 on the basket end effector 301 may be multi-purpose, while other electrodes are single-purpose. For example, some of the electrodes may function as both navigation and electrophysiology mapping electrodes, others may function only as electrophysiology mapping electrodes, and yet other electrodes may function only as navigation electrodes.

As shown in FIG. 3B, four splines $310_{1,3,5,7}$ are rotated relative to the remaining four splines $310_{2,4,6,8}$ to create high-density array regions $312_{1-2}$. The high-density array regions may be used for regional mapping of areas of interest. Global mapping of a cardiac chamber, for example, is often followed by regional mapping using another catheter. The present basket catheter 301' is capable of performing both global and regional mapping operations by adjusting the electrode array density via the high-density array regions $312_{1-2}$. Actuation of the moveable splines $310_{1,3,5,7}$ may be accomplished via a clinician's input on a catheter handle. Upon completion of a regional electrophysiology mapping, the moveable splines $310_{1,3,5,7}$ may be returned to respective positions for global mapping (as shown in FIG. 3A). In various embodiments of the present disclosure, one or more of the splines 310 may be rotatably adjusted to facilitate more or less electrode array density. Moreover, in some embodiments matched splines opposite one another (e.g., splines $310_{2,6}$) may be independently adjustable, or in other implementations may be dependent and actuated simultaneously.

Figure 3C:
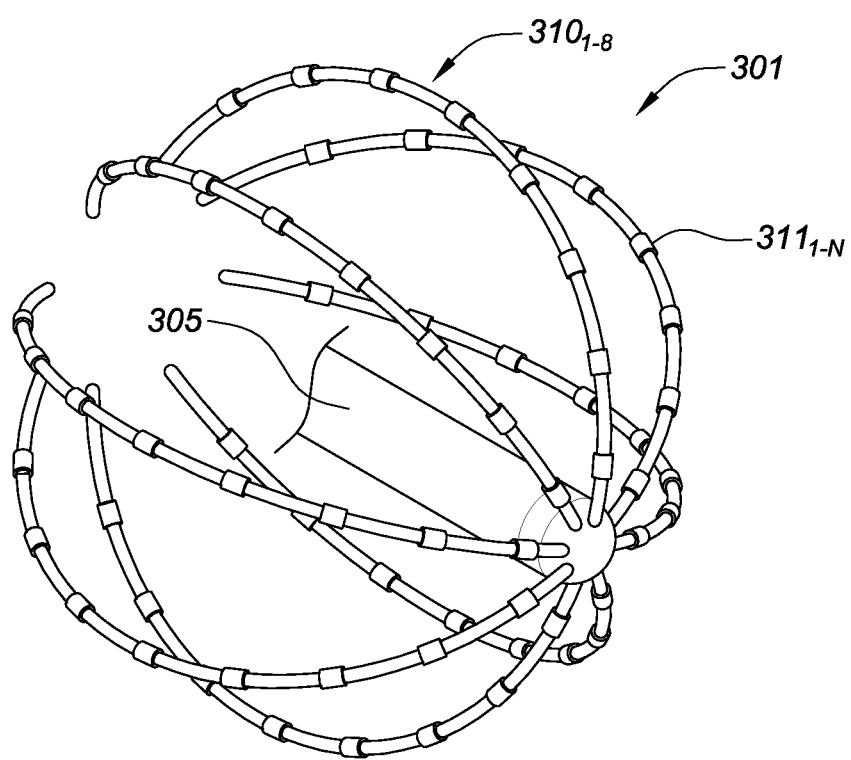
FIG. 3C is an isometric side view of the basket end effector of FIG. 3A with the basket struts inverted, consistent with various embodiments of the present disclosure.

FIG. 3C is an isometric side view of a basket end effector 301 comprised of a plurality of splines $310_{1-8}$ which are coupled to a catheter shaft 305 at a distal end and free at a proximal end. In FIG. 3C, the basket splines $310_{1-8}$ are inverted. While the present embodiment presents a basket comprised of eight splines $310_{1-8}$, basket catheters with three or more splines are readily envisioned. To facilitate expansion/contraction of the basket, the splines $310_{1-8}$ may be comprised of a shape-memory alloy (e.g., nitinol) which returns to a semi-circular shape after exiting an introducer. In yet other embodiments, each of the splines may be coupled to one or more steering wires which when actuated steer the splines to form the desired shape.

The inverted configuration of splines $310_{1-8}$ allows for catheter shaft 305 to be positioned near a distal end of the basket end effector 301, facilitating more precise positioning of the basket end effector 301. Moreover, distal most electrodes 311 are positioned on the splines 310 near a coupling point to the catheter shaft 305. As a result, the distal most electrodes are less susceptible to spline flexing that may otherwise negatively impact electrode-tissue contact during electrophysiology diagnostics.

Figure 4A:
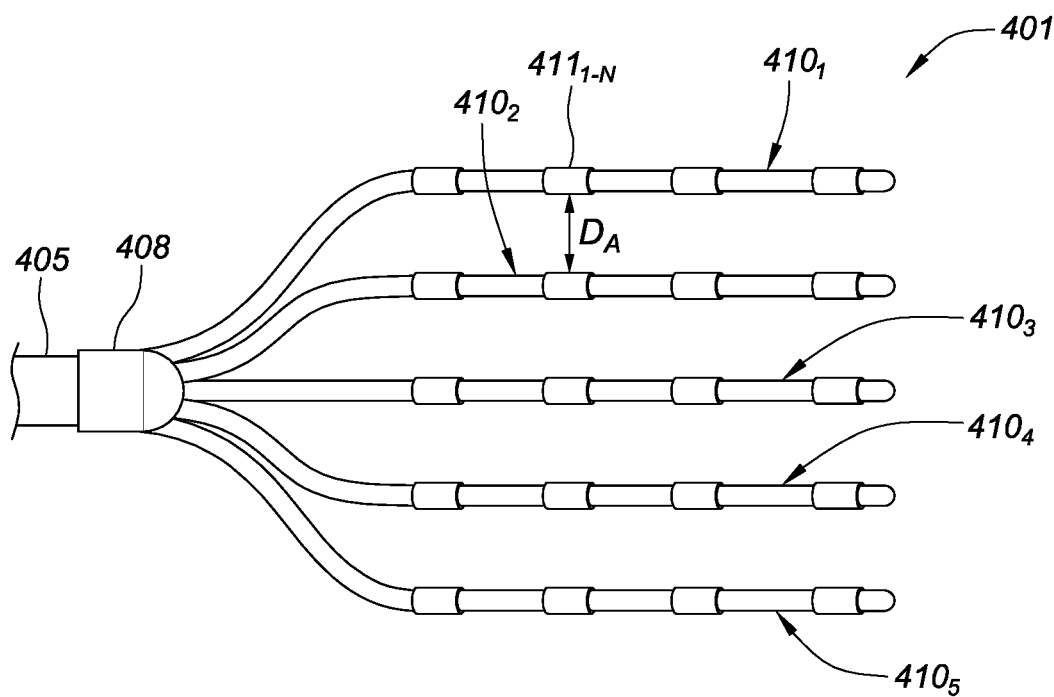
FIG. 4A is an isometric, top view of a planar end effector of an electrophysiology mapping catheter configured for regional mapping, consistent with various embodiments of the present disclosure.
Figure 4B:
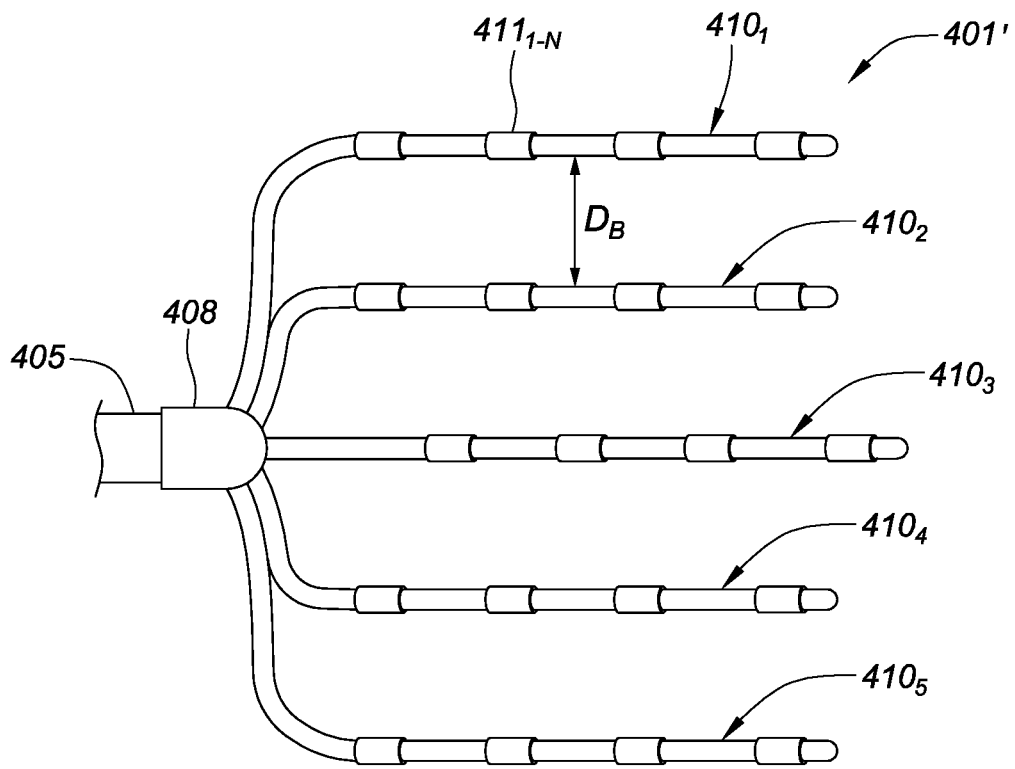
FIG. 4B is an isometric, top view of the planar end effector of FIG. 4A with the splines laterally extended to conduct global mapping, consistent with various embodiments of the present disclosure.

FIG. 4A is an isometric, top view of a planar end effector 401 of an electrophysiology mapping catheter configured for regional mapping (a first configuration), FIG. 4B is an isometric, top view of the planar end effector 401' of FIG. 4A, with struts $410_{1-5}$ laterally extended to conduct global mapping (a second configuration).

The planar array 401 of an electrophysiology mapping catheter includes a high-density array of electrodes $411_{1-N}$, consistent with various embodiments of the present disclosure. The planar array 401 forms a flexible array of the electrodes $411_{1-N}$. This array of electrodes is coupled to a flexible framework of struts $410_{1-5}$ which extend in a plane that is substantially parallel with a longitudinal axis of catheter shaft 405. Each of the struts is precisely, laterally separated from each other to facilitate exact spacing between electrodes $411_{1-N}$ on adjacent struts $410_{1-5}$, and the struts are coupled to one another at respective proximal ends (e.g., at a bushing 408) and free at respective distal ends.

As shown in FIG. 4A, each of the five struts $410_{1-5}$ may carry a plurality of electrodes 411, with the spacing of the electrodes along a length of the strut being the same (or at least known). Similarly, the spacing between electrodes 411 across struts 410 of the array may also be equal (or at least known). The result is a plurality of electrode bipole pairs with known spacing.

Although the planar array 401 in FIG. 4A depicts five struts $410_{1-5}$, the catheter may comprise more or less struts, with spacing between each respective strut based on a desired electrode spacing for a given electrophysiology application. Additionally, while the planar array 401 depicted in FIG. 4A has 20 electrodes 411, the planar array may include more or fewer than 20 electrodes, and each strut need not have the same number of electrodes as adjacent struts.

In some embodiments, the electrodes $411_{1-N}$ may be used in diagnostic, therapeutic, and/or mapping procedures. For example and without limitation, the electrodes 411 may be used for electrophysiological studies, pacing, cardiac mapping, and ablation. In some embodiments, the electrodes 411 may perform unipolar or bipolar ablation (e.g., via the use of bipole pairs of electrodes). This unipolar or bipolar ablation may create specific lines or patterns of lesions. In some embodiments, the electrodes 411 may receive electrical signals from the heart, which can be used for electrophysiological studies/mapping. Importantly, as the electrode spacing between adjacent electrodes on a strut 410, and those on adjacent struts, are the same (or otherwise known), bipole pairs with varying relative orientations may be sampled to determine electrical characteristics of the tissue in contact with the bipole pairs. The sampled electrical characteristics may be processed to remove catheter orientation-based signal effects. In some embodiments, the electrodes 411 may perform a location or position sensing function related to cardiac mapping (e.g., determine location and/or orientation of the catheter 401).

The planar array 401 may be adapted to conform to tissue (e.g., cardiac tissue). For example, when the planar array contacts tissue, each strut 410$_{1-5}$ may independently deflect to conform to the tissue. The ability for the planar array to deflect in response to tissue may be particularly beneficial when the planar array comes into contact with contoured, irregular, or trabeculated tissue. In some embodiments, the struts 410 (or the understructure of the struts) may be constructed from a flexible or spring-like material such as nitinol and/or a flexible substrate.

While various embodiments of the planar array 401 disclosed in the present disclosure are depicted with ring electrodes 411$_{1-N}$ coupled to the struts 410$_{1-5}$, embodiments with spot-type electrodes coupled to the struts are readily envisioned. Moreover, in yet further embodiments, the struts of the planar array may comprise flexible thin films compatible with printed circuit manufacturing techniques and/or have such thin films coupled to structural elements of the strut (e.g., nitinol-based structural elements). In such embodiments, spot-type electrodes may be printed onto the struts themselves. In flexible printed circuit embodiments of the present disclosure, the printed electrodes may be electrically coupled to signal processing circuitry and/or driver circuitry via traces extending on or within the one or more thin film layers.

In some embodiments of the present disclosure, a planar array 401 may include steering wires which extend a length of catheter shaft 405. Prior to reaching a bushing 408 that couples the catheter shaft 405 to struts 410$_{1-5}$ of planar array 401, the steering wires may be coupled to pull rings which receive a force transmitted from a proximal end of the steering wires and facilitates steering the catheter shaft 405 and the planar array 401 through a patient's vasculature. As further shown in FIG. 4A, each of the struts 410$_{1-5}$ includes a plurality of electrodes 411$_{1-N}$ distributed along a length of the struts. In the present embodiment, each of the electrodes are equally spaced ($D_A$) from each of the adjacent electrodes. When controller circuitry samples electrical signals from bipole pairs of electrodes within the planar array 401, each of the bipole pairs will detect various electrical characteristics indicative of the tissue health in contact with the electrodes. The five struts 410$_{1-5}$ are designed to maintain the electrodes 411$_{1-N}$ in a spaced relationship so that each bipole pair of electrodes capture electrophysiology data of tissue across a known distance.

As shown in a second configuration, planar array 401' of FIG. 4B includes struts 410$_{1-5}$ which have been actuated by a clinician. The actuation changes a distance between electrodes 411$_{1-N}$ on adjacent struts from $D_A$ to $D_B$ (where $D_B$ is a known distance). Of course, the distance between electrodes running along a length of the struts 410 will not change in response to the actuation. The change in electrode spacing between adjacent struts facilitates variable granularity electrophysiology mapping of target tissue. The deflection of the struts facilitates a more global mapping of target tissue, at least laterally relative to a longitudinal axis of the catheter.

Figure 5A:
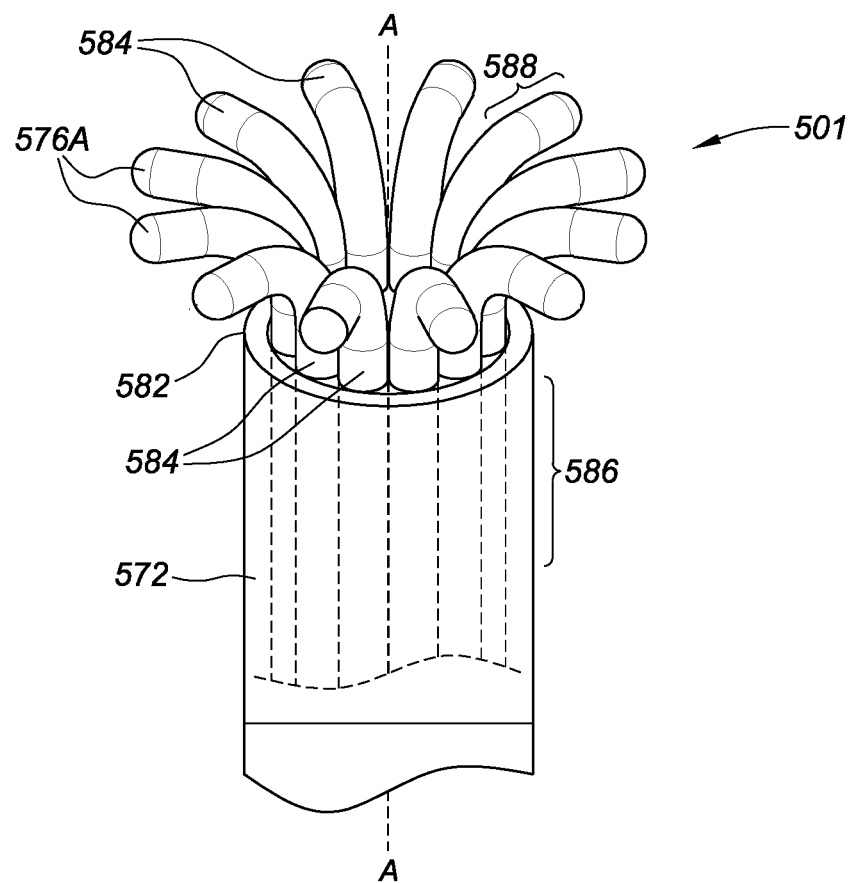
FIG. 5A is an isometric side view of a plurality of deployed catheterlets extending from a distal end of an electrophysiology mapping catheter and configured for global mapping, consistent with various embodiments of the present disclosure.

FIG. 5A is an isometric side view of a plurality of deployed catheterlets 576A, extending from a distal end 582 of an electrophysiology mapping catheter 501, and configured for global mapping.

In FIG. 5A, a distal portion 588 of each of the catheterlets 576A forms an "L" shape when the distal portions are extended beyond sheath 572. In this embodiment, the catheterlets 576A have a proximal portion 586 that is generally parallel with a longitudinal axis of sheath 572 (and further defined by axis A-A), and the distal portions of the catheterlets extending perpendicular to the sheath when the catheterlet is fully extended. This catheterlet configuration creates an angle of approximately 90°. Accordingly, distal portions 588 of each catheterlet and the corresponding electrodes 584 thereon are positioned on a plane that extends perpendicular relative to axis A-A.

The plurality of catheterlets 576A may flex to accommodate the variations of complex endocardial topologies such as the antrum and ostium of pulmonary veins. The flexibility of the plurality of catheterlets 576A facilitate "one-shot" ablation treatment of tissue (e.g., for pulmonary vein isolation). The electrodes 584 may also be utilized for electrophysiological diagnostics. To facilitate the topologies of various patients, the extension of the catheterlets 576A may be varied (e.g., partially or fully deployed) to suit a given patient's anatomy. Moreover, each catheterlet may flex in response to an irregular surface, thereby facilitating improved tissue contact across an entire electrode array.

Each of the plurality of catheterlets 576A may include one or more electrodes 584. The electrodes may be used for electrophysiology mapping and/or delivering ablation therapy to tissue. In some embodiments, the catheterlets may include more than one electrode. For example, a secondary electrode 584 may be positioned proximally along the catheterlet. The secondary electrode 584, when extended into contact with tissue, may further facilitate electrophysiology mapping and/or delivering ablation therapy to tissue. Alternatively, the secondary electrode 584 may function as a localization electrode to facilitate magnetic-based, impedance-based, or hybrid-type catheter localization.

As shown in FIG. 5A, electrophysiology mapping catheter 501 is configured in a first configuration for global electrophysiology mapping of a region. However, in some applications it may be further desirable to conduct regional electrophysiology mapping of tissue without necessitating an entirely different catheter.

Figure 5B:
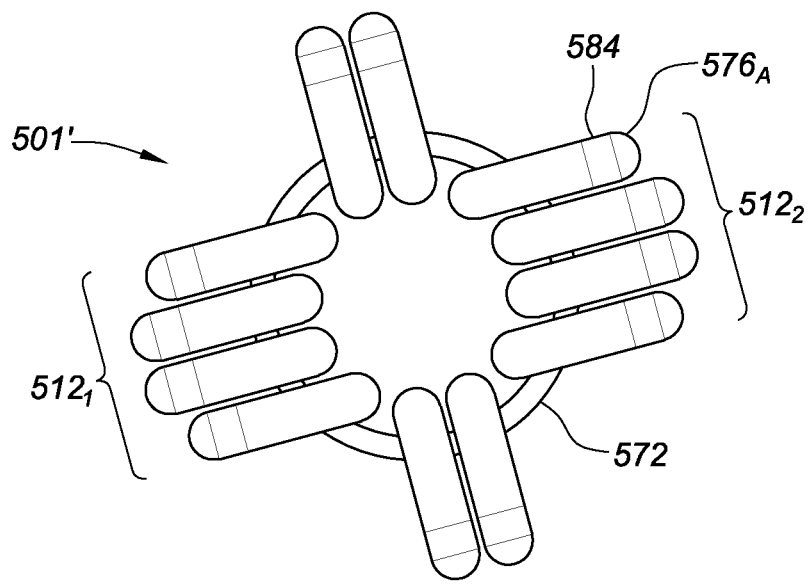
FIG. 5B is a top view of the of the plurality of deployed catheterlets of FIG. 5A and configured for regional mapping, consistent with various embodiments of the present disclosure.

FIG. 5B is a top view of the of the plurality of deployed catheterlets of FIG. 5A configured for regional mapping (a second configuration 501'). In FIG. 5B, a number of catheterlets 576A have been rotated relative to an axis A-A to form high-density array regions 512$_{1-2}$. In the high-density array regions, two or more catheterlets (and thereby their respective electrodes 584) are placed in close proximity. In these high-density array regions, increased electrophysiology mapping density may be achieved.

Figure 6A:
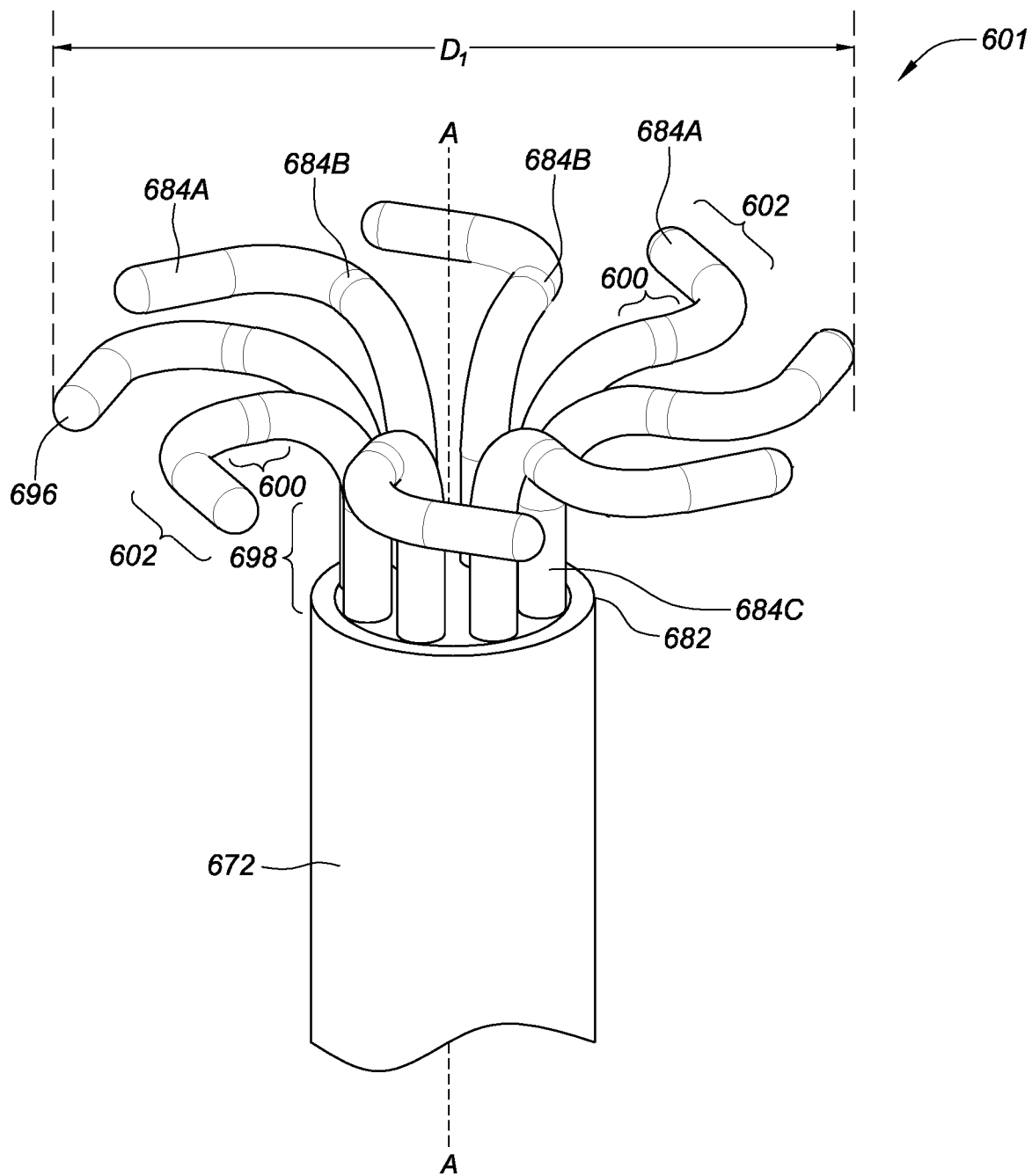
FIG. 6A is an isometric side view of a plurality of deployed catheterlets extending from a distal end of an electrophysiology mapping catheter, the catheterlets configured for global mapping, consistent with various embodiments of the present disclosure.

FIG. 6A is an isometric side view of a plurality of deployed catheterlets 696 extending from a distal end 682 of an electrophysiology mapping catheter 601, the catheterlets configured for global mapping, consistent with various embodiments of the present disclosure. When deployed, the mapping catheter 601, in the global mapping configuration, has a diameter of $D_1$.

In FIG. 6A, a distal portion 602 of each catheterlet 696 forms an "L" shape with an intermediary region 600 when the catheterlets are extended beyond sheath 672. The distal portions and intermediary regions of each catheterlet extend along a plane that is substantially perpendicular to a proximal portion 698 (and further defined by axis A-A) when the catheterlets are extended from the sheath. Accordingly, distal portion 602 and intermediary region 600 of each catheterlet are positioned on a plane that extends perpendicular relative to axis A-A.

The plurality of compound catheterlets 696 may flex to accommodate the variations of complex endocardial topologies. The flexibility of the plurality of catheterlets 696 may allow for "one-shot" ablation treatment of tissue via electrodes 684A. Electrodes 684A on distal portion 602 of each catheterlet 696 may also be utilized for electrophysiological diagnostics. To facilitate the topologies of various patients, the extension of the catheterlets 696 may be varied (e.g., partially or fully deployed) to suit a given patient's anatomy. Moreover, each catheterlet may flex in response to an irregular surface, thereby facilitating improved tissue contact across an entire electrode array.

Each of the plurality of catheterlets 696 may include one or more electrodes. For example, in the present embodiment distal portion 602 may include one or more electrodes 684A, and intermediary region 600 may include one or more electrodes 684B. The electrodes may be used for electrophysiology mapping and/or delivering ablation therapy to tissue. In some specific embodiments, electrodes 684A may be used to conduct an ablation therapy and/or electrophysiology diagnostics, and the electrodes 684B may also be used to conduct electrophysiology diagnostics. The catheterlets may further include a third electrode 684C. The third electrode 684C may function as a localization electrode to facilitate localization of a distal tip of the catheter 601 within a magnetic-based, impedance-based, or hybrid-type catheter localization system.

Figure 6B:
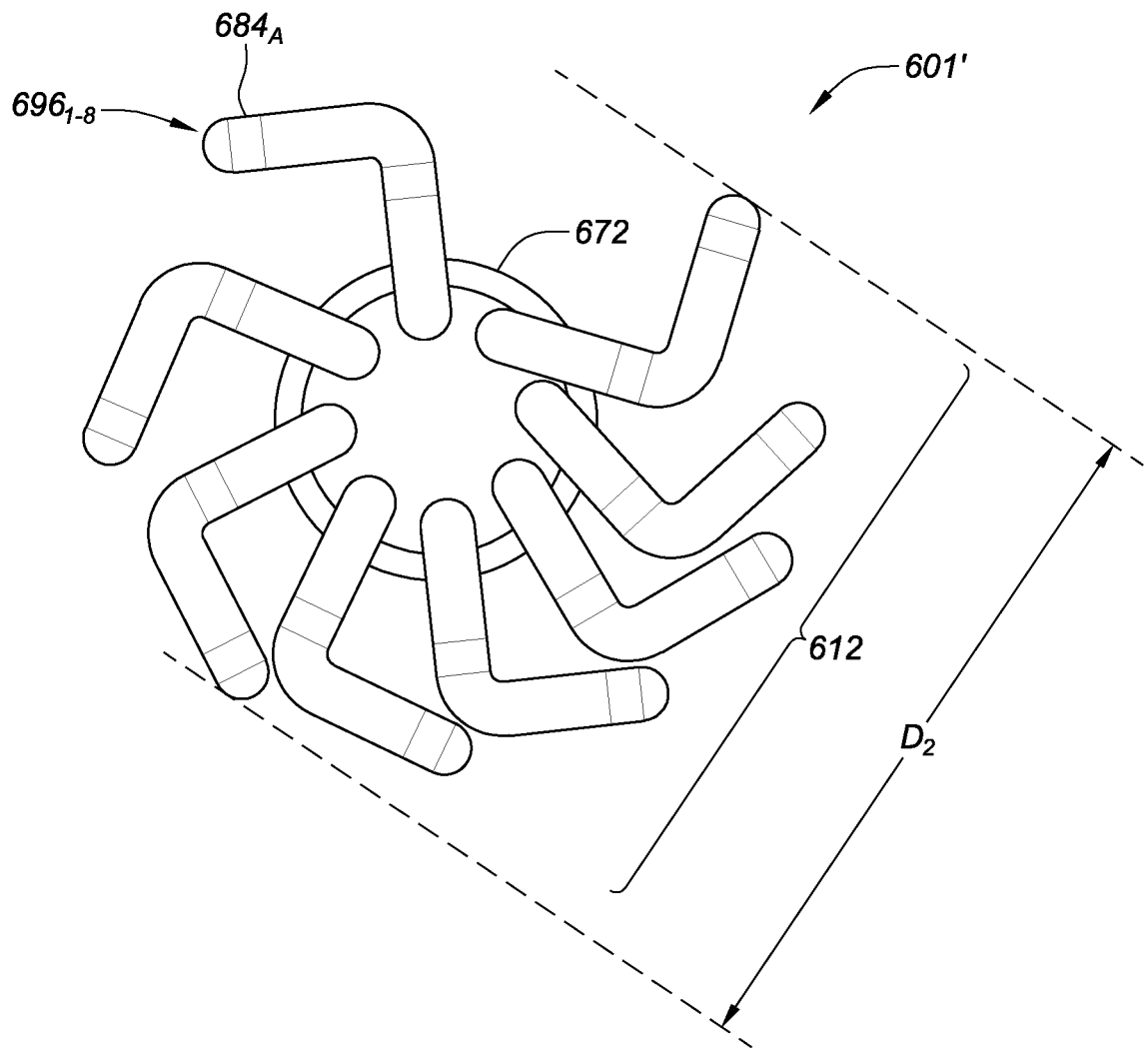
FIG. 6B is a top view of the of the plurality of deployed catheterlets of FIG. 6A, the catheterlets configured for regional mapping, consistent with various embodiments of the present disclosure.

As shown in FIG. 6A, electrophysiology mapping catheter 601 is configured in a first configuration for global electrophysiology mapping of a region. However, in some applications it may be further desirable to conduct regional electrophysiology mapping of tissue without necessitating an entirely different catheter. FIG. 6B is a top view of the of the plurality of deployed catheterlets of FIG. 6A, the catheterlets configured for regional mapping (a second configuration 601'). In this second, regional mapping configuration, the mapping catheter has a diameter of $D_2$, which is less than $D_1$.

In FIG. 6B, a number of catheterlets 696 have been rotated relative to the axis A-A to form high-density array region 612. In the high-density array region, two or more catheterlets (and thereby their respective electrodes 684A) are placed in close proximity. In this high-density array region, increased electrophysiology mapping density may be achieved. As discussed above in reference to FIG. 5B, the embodiment of FIG. 6B may be further configured to have two or more high-density array regions.

U.S. provisional application No. 62/414,634, filed 28 Oct. 2016, U.S. provisional application No. 62/572,186, filed 13 Oct. 2017, and U.S. application Ser. No. 15/793,093, filed 25 Oct. 2017 are all generally directed to flexible, high-density mapping catheters and are incorporated by reference as though fully set forth herein.

While various embodiments of high-density electrode catheters are disclosed herein, the teachings of the present disclosure may be readily applied to various other catheter embodiments as disclosed, for example, in the following patents and patent applications which are hereby incorporated by reference: U.S. provisional application No. 61/753,429, filed 16 Jan. 2013; U.S. provisional application No. 60/939,799, filed 23 May 2007; U.S. application Ser. No. 11/853,759 filed 11 Sep. 2007, now U.S. Pat. No. 8,187,267, issued 29 May 2012; U.S. provisional application No. 60/947,791, filed 3 Jul. 2007; U.S. application Ser. No. 12/167,736, filed 3 Jul. 2008, now U.S. Pat. No. 8,206,404, issued 26 Jun. 2012; U.S. application Ser. No. 12/667,338, filed 20 Jan. 2011 (371 date), published as U.S. patent application publication no. US 2011/0118582 A1; U.S. application Ser. No. 12/651,074, filed 31 Dec. 2009, published as U.S. patent application publication no. US 2010/0152731 A1; U.S. application Ser. No. 12/436,977, filed 7 May 2009, published as U.S. patent application publication no. US 2010/0286684 A1; U.S. application Ser. No. 12/723,110, filed 12 Mar. 2010, published as U.S. patent application publication no. US 2010/0174177 A1; U.S. provisional application No. 61/355,242, filed 16 Jun. 2010; U.S. application Ser. No. 12/982,715, filed 30 Dec. 2010, published as U.S. patent application publication no. US 2011/0288392 A1; U.S. application Ser. No. 13/159,446, filed 14 Jun. 2011, published as U.S. patent application publication no. US 2011/0313417 A1; international application no. PCT/US2011/040629, filed 16 Jun. 2011, published as international publication no. WO 2011/159861 A2; U.S. application Ser. No. 13/162,392, filed 16 Jun. 2011, published as U.S. patent application publication no. US 2012/0010490 A1; U.S. application Ser. No. 13/704,619, filed 16 Dec. 2012, which is a national phase of international patent application no. PCT/US2011/040781, filed 16 Jun. 2011, published as international publication no. WO 2011/159955 A1.

Additional information and examples can be found in U.S. provisional application 62/681,928 filed Jun. 7, 2018; which is hereby incorporated by reference as if fully disclosed herein.

While various embodiments of the present disclosure are directed to the use of high-density electrode catheters in conjunction with OIS/OT algorithms, the teachings of the present disclosure may be readily applied to various other algorithm types. For example, embodiments consistent with the present disclosure may utilize the electrode signal post-processing techniques, and electrophysiology mapping algorithms disclosed in the following publications, which are hereby incorporated by reference: Magtibay et al. JAHA 2017 (J Am Heart Assoc. 2017; 6:e006447. DOI: 10.1161/JAHA.117.006447)(see, e.g., pages 6 and 7, and section titled "Omnipoles Provide the Largest Possible Bipolar Voltages"); and Haldar et al. Circulation AE 2017 (Circ Arrhythm Electrophysiol. 2017; 10:e005018. DOI: 10.1161/CIRCEP.117.005018)(see, e.g., page 6, section titled "Omnipolar Voltage Amplitude Correlates to Largest Measurable Bipolar Vpp," and FIG. 4).

Various embodiments presented herein are amenable to the application of spot electrodes coupled to a flexible electronic circuit, where the flexible electronic circuit may also (partially) comprise the splines and struts of the planar and basket catheters, respectively. Yet other embodiments may be directed to the use of ring electrodes crimped or swagged on to splines and struts, and comprising well-known materials in the art. The ring electrodes being electrically coupled to signal processing circuitry using lead wires. The ring electrodes positioned along the splines and struts form bipole pairs of electrodes with known spacing therebetween. In yet other embodiments, ring electrodes may be swagged or crimped on to a flexible circuit board comprising at least part of the splines, and/or struts of the various catheters disclosed herein.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A planar array catheter comprising:
    an elongated catheter shaft including a proximal end and a distal end, and defining a longitudinal axis;
    a flexible, planar array coupled to the distal end of the catheter shaft, wherein the planar array is configured to conform to tissue and includes two or more struts extending substantially parallel with the longitudinal axis and lying in a common plane, each of the two or more struts having a plurality of electrodes mounted thereon,
    wherein the planar array is further configured with an adjustable relative spacing between the two or more struts and thereby a variable areal density of the plurality of electrodes, wherein in a first configuration, the plurality of electrodes are equally spaced along both a length of each of the two or more struts and across the two or more struts and in a second configuration, the spacing of electrodes of the plurality of electrodes across the two or more struts is greater than the spacing of electrodes of the plurality of electrodes along the length of each of the two or more struts;
    a catheter handle coupled to the proximal end of the elongate catheter shaft; and
    a pullwire that extends through a lumen within the catheter shaft and one of the two or more struts of the planar array, the pullwire coupled to the catheter handle and a distal end of the planar array, wherein the pullwire is configured to respond to actuation of the pullwire by a clinician at the catheter handle to manipulate the plurality of electrodes between the first and second configurations.

2. The planar array catheter of claim 1, wherein one or more of the plurality of electrodes are spot electrodes and one or more of the struts include flexible electronic circuit boards that are communicatively and mechanically coupled to the plurality of electrodes.

3. The planar array catheter of claim 1, wherein each of the electrodes of the plurality of electrodes are independently addressable relative to the other electrodes of the plurality of electrodes, wherein the center-to-center distance between adjacent electrodes of the plurality of electrodes is between 0.1 and 4 millimeters, and the plurality of electrodes are configured to sample electrical characteristics of contacted tissue in at least two substantially transverse directions.

4. The planar array catheter of claim 1, wherein the plurality of electrodes are configured to collect electrical characteristics of the tissue in contact with the planar array catheter, and the collected electrical characteristics of the tissue are independent of the orientation of the planar array catheter relative to the tissue.

5. The planar array catheter of claim 1, wherein the plurality of electrodes are configured to sample electrical characteristics of the contacted tissue, and the sampled electrical characteristics are collectively indicative of the electrical characteristics of the contacted tissue, independent of the orientation of the planar array catheter relative to the tissue.

6. The planar array catheter of claim 1, wherein the plurality of electrodes includes bipole electrode pairs that include electrodes on adjacent struts of the planar array.

7. The planar array catheter of claim 1, wherein the plurality of electrodes includes bipole electrode pairs that extend diagonally across adjacent struts of the planar array.

8. The planar array catheter of claim 6, wherein the bipole electrode pairs are configured to sample electrical characteristics of the contacted tissue, and the samples are collectively indicative of the electrical characteristics of the contacted tissue, independent of the orientation of the planar array catheter relative to the tissue.

\* \* \* \* \*